|                                               | US006387875B1 |
|-----------------------------------------------|---------------|

(12) United States Patent
Nicola et al.

(10) Patent No.: US 6,387,875 B1
(45) Date of Patent: *May 14, 2002

(54) METHOD OF USE FOR MURINE LEUKAEMIA INHIBITORY FACTOR-BINDING PROTEIN (MLBP)

(75) Inventors: Nicos Anthony Nicola, Mount Albert; Meredith Layton, Tecoma; Donald Metcalf, Balwyn; Richard J Simpson, Richmond, all of (AU)

(73) Assignee: Amrad Corporation Limited, Victoria (AU)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/331,650
(22) PCT Filed: Jul. 1, 1993
(86) PCT No.: PCT/AU93/00325
 § 371 Date: Nov. 10, 1994
 § 102(e) Date: Nov. 10, 1994
(87) PCT Pub. No.: WO94/01464
 PCT Pub. Date: Jan. 20, 1994

(30) Foreign Application Priority Data

Jul. 1, 1992 (AU) .............................................. PL 3265

(51) Int. Cl.$^7$ ................................................ A61K 38/19
(52) U.S. Cl. ................................ 514/2; 514/8; 514/13; 514/21
(58) Field of Search ................................ 435/69.1, 69.5, 435/69.7, 70.1, 320.1; 514/2, 13, 8, 21; 530/326, 350; 536/23.4, 23.5

(56) References Cited

U.S. PATENT DOCUMENTS 5,187,077 A * 2/1993 Gearing et al.

OTHER PUBLICATIONS

Gearing et al., *Embo J.*, vol. 10, pp. 2839–2848, 1991.*

* cited by examiner

*Primary Examiner*—Gary L. Kunz
*Assistant Examiner*—Stephen Gucker
(74) *Attorney, Agent, or Firm*—Scully, Scott, Murphy & Presser

(57) ABSTRACT

The present invention relates to a isolated leukaemia inhibitory factor (LIF)-binding protein (LBP) in soluble form and obtainable from a first mammalian species, said LBP capable of inhibiting the ability of LIF from a second mammalian species to induce differentiation of M1 myeloid leukaemic cells in vitro to a greater extent when compared to its ability to inhibit LIF from said first mammalian species.

2 Claims, 15 Drawing Sheets

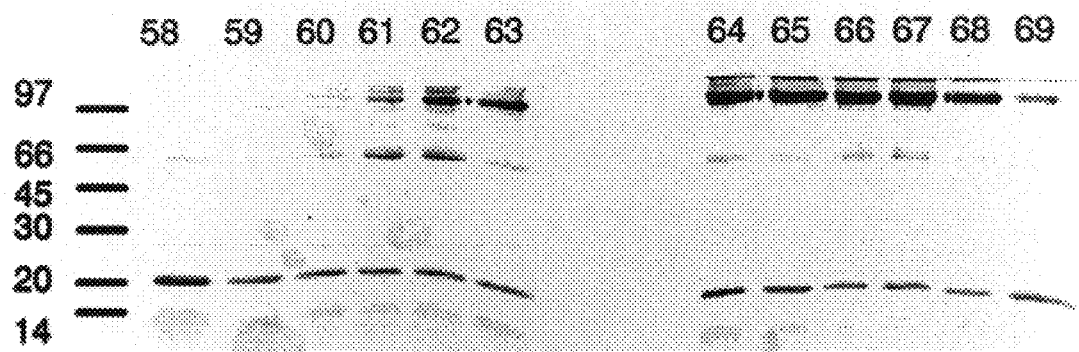
FIG. IIA

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 23 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:1:

Gly Val Gln Asp Leu Lys Cys Thr Thr Asn Asn Met Arg Val Trp Asp
1            5                 10                15

-continued

```
Cys Thr Trp Pro Ala Pro Leu
         20
```

METHOD OF USE FOR MURINE LEUKAEMIA INHIBITORY FACTOR-BINDING PROTEIN (MLBP)

The present invention relates to a Leukaemia Inhibitory Factor-Binding Protein (LBP) and more particularly to a soluble LBP, uses thereof and compositions containing same.

Leukaemia Inhibitory Factor (LIF) is a polyfunctional glycoprotein with actions on a broad range of tissue and cell types, including induction of differentiation in a number of myeloid leukaemic cell lines, suppression of differentiation in normal embryonic stem cells, stimulation of proliferation of osteoblasts and DA-1 haemopoietic cells and potentiation of the proliferative action of interleukin-3 (IL-3) on megakaryocyte precursors. Functionally, it is able to switch autonomic nerve signalling from adrenergic to cholinergic mode, stimulate calcium release from bones, stimulate the production of acute phase proteins by hepatocytes and induce loss of fat deposits by inhibiting lipoprotein lipase-mediated lipid transport into adipocytes[1].

This array of actions is puzzling since it is difficult to conceive of any situation that would require a coordinated response in all the known target tissues of LIF. Actions of LIF, therefore, are probably designed to be restricted by co-localisation of LIF-producing cells and LIF-responsive cells, with tight regulation of LIF production. However, such an arrangement is likely to result in some release of LIF into the circulatory system including blood and other bodily fluids.

In work leading up to the present invention, the inventors discovered a LIF-binding protein in serum which is capable of inhibiting the biological activity of LIF. The identification of this LIF antagonist will now permit greater control in LIF therapy and to prevent any systemic effects of locally administered LIF which are not therapeutically desirable. It also provides a new agent useful in the treatment of LIF associated diseases or conditions. In a particular embodiment, the inventors have discovered that the inhibitory effect of the LIF-binding protein may be more pronounced in heterologous systems, i.e. where the LIF-binding protein from one mammal is used to inhibit LIF in another mammal.

Accordingly, one aspect of the present invention provides a LIF-binding protein (LBP) in soluble form and isolatable from a mammal.

More particularly, the present invention is directed to an isolated LBP in soluble form and obtainable from a first mammalian species, said LBP capable of inhibiting the ability of LIF from a second mammalian species to induce differentiation of M1 myeloid leukaemic cells in vitro to a greater extent when compared to its ability to inhibit LIF from said first mammalian species.

The isolated LBP is preferably biologically pure meaning that it represents at least 20%, preferably at least 50%, even more preferably at least 70% and still more preferably at least 85% of the molecule in a solution or composition as determined by weight, biological activity or other convenient means of measurement. Notwithstanding that the LBP is isolated, it may also be in the form of a composition. According to this aspect of the present invention there is contemplated a composition comprising an LBP in soluble form and obtainable from a first mammalian species, said LBP capable of inhibiting the ability of LIF from a second mammalian species to induce differentiation of M1 myeloid leukaemic cells in vitro to a greater extent when compared to its ability to inhibit LIF from said first mammalian species, said composition substantially free of protein molecules not having LBP properties.

The isolated LBP in soluble form and obtainable from the first mammalian species is further characterised in that the LBP has at least a 100 fold higher binding affinity for a LIF from the second mammalian species compared to the binding affinity for a LIF from said first mammalian species.

In accordance with the present invention, the first mammal is preferably a human, mouse or rat or other rodent, pig, cow, sheep or other ruminant, goat, horse or primate. The second mammal may also be a human, mouse or rat or other rodent, pig, cow, sheep or other ruminant, goat, horse or primate. Preferably, the first mammal is a non-human mammal and the second mammal is a human. Most preferably, the first mammal is a mouse and the second mammal is a human.

Accordingly, in a preferred embodiment, the present invention is directed to a LBP in soluble form isolatable from a murine animal. More particularly, the present invention provides a LBP in soluble form isolatable from a murine animal, said LBP capable of greater inhibition of human LIF compared to murine LIF.

The isolated LBP may be the naturally occurring molecule, a naturally occurring derivative, part or fragment thereof or may be a recombinant or synthetic form of the molecule including any recombinant or synthetic derivatives, parts or fragments thereof. The LBP may be naturally glycosylated, partially glycosylated or unglycosylated or may have an altered glycosylation pattern from the naturally occurring molecule. The molecule may, for example, undergo treatment with N-glycanase resulting in a deglycosylated or substantially deglycosylated molecule. A "derivative" of LBP is considered herein to generally comprise a single or multiple amino acid insertion, deletion and/or substitution of amino acid residues relative to the naturally occurring sequence or an insertion, deletion and/or substitution of molecules associated with LBP such as carbohydrate moieties. A "derivative" is also considered to be a molecule with at least 45% amino acid sequence similarity to the amino acid sequence of the LBP.

Amino acid insertional derivatives of LBP include amino and/or carboxyl terminal fusions as well as intra-sequence insertions of single or multiple amino acids. Insertional amino acid sequence variants are those in which one or more amino acid residues are introduced into a predetermined site in the protein although random insertion is also possible with suitable screening of the resulting product. Deletional variants are characterised by the removal of one or more amino acids from the sequence. Substitutional amino acid variants are those in which at least one residue in the sequence has been removed and a different residue inserted in its place. Typical subsitutions are those made in accordance with the following Table 1:

TABLE 1

Suitable residues for amino acid substitutions

| Original Residue | Exemplary Substitutions |
| --- | --- |
| Ala | Ser |
| Arg | Lys |
| Asn | Gln; His |
| Asp | Glu |
| Cys | Ser |
| Gln | Asn |
| Glu | Ala |
| Gly | Pro |

TABLE 1-continued

Suitable residues for amino acid substitutions

| Original Residue | Exemplary Substitutions |
| --- | --- |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Where the LBP is derivatised by amino acid substitution, the amino acids are generally replaced by other amino acids having like properties, such as hydrophobicity, hydrophilicity, electronegativity, bulky side chains and the like. Amino acid substitutions are typically of single residues. Amino acid insertions will usually be in the order of about 1–10 amino acid residues and deletions will range from about 1–20 residues. Preferably, deletions or insertions are made in adjacent pairs, i.e. a deletion of two residues or insertion of two residues.

The amino acid variants referred to above may readily be made using peptide synthetic techniques well known in the art, such as solid phase peptide synthesis[14] and the like, or by recombinant DNA manipulations. Techniques for making substitution mutations at predetermined sites in DNA having known or partially known sequence are well known and include, for example, M13 mutagenesis. The manipulation of DNA sequences to produce variant proteins which manifest as substitutional, insertional or deletional variants are conveniently described, for example, in Maniatis et al[15].

Other examples of recombinant or synthetic mutants and derivatives of the LBP of the present invention include single or multiple substitutions, deletions and/or additions of any molecule associated with the LBP such as carbohydrates, lipids and/or proteins or polypeptides.

In one embodiment, the LBP is truncated at its carboxy terminal end portion to render said LBP soluble.

In another embodiment, the LBP is a fusion molecule between LBPs from said first and second mammalian species.

According to this embodiment, there is provided a fusion polypeptide defining an LBP, said fusion polypeptide comprising first and second amino acid sequences wherein said first amino acid sequence is derivable from an LBP from a first mammalian species and said second amino acid sequence is derivable from an LBP from a second mammalian species wherein the LBP from said first mammalian species is capable of inhibiting the ability of LIF from said second mammalian species to induce differentiation of M1 myeloid leukaemic cells in vitro to a greater extent when compared to its ability to inhibit LIF from said first mammalian species such that said fusion polypeptide retains the ability to inhibit LIF from said second mammalian species to a greater extent than LIF from said first mammalian species.

In a preferred embodiment, the first mammalian species is a mouse, rat or other rodent, pig, cow, sheep or other ruminant, goat, horse or primate and said second mammalian species is a human. Most preferably, the first mammalian species is a mouse and the fusion polypeptide is referred to as a "humanised" form of the mouse LBP. Such molecules are particularly advantageous in avoiding or reducing possible induction of an antigenic immune response by administering to said first mammal, an LBP from said second mammal.

According to this most preferred aspect of the present invention, there is provided a fusion polypeptide defining an LBP, said fusion polypeptide comprising first and second amino acid sequences wherein said first amino acid sequence is derivable from an LBP from a mouse and said second amino acid sequence is derivable from an LBP from a human wherein said fusion polypeptide is capable of inhibiting the ability of LIF from a human to induce differentiation of M1 myeloid leukaemic cells in vitro to a greater extent when compared to its ability to inhibit mouse LIF and wherein administration of said fusion polypeptides into a human results in a substantially reduced immune response against said fusion polypeptide compared to the administration to said human of native or recombinant mouse LBP. Conveniently, an "immune response" is measured by titre of antibodies specific to a molecule and/or involve extent of a cellular immune response.

The fusion polypeptides can be prepared by a range of suitable methods but conveniently is by a method similar to the method employed by the inventors to map the site on the hLIF molecule that confers both binding to the hLIF receptor α-chain and the unusual high affinity binding to the mouse LIF receptor α-chain (mLBP) similar to that described in the experiment summarised in FIG. 9. In particular, a hLBP molecular frame work is used to construct a series of mouse-human mLBP chimaeric molecules in order to determine the minimum number of hLIF amino acid residues that is necessary to substitute into the hLBP sequence in order to create a molecule that has the properties that are peculiar to hLBP.

Reference in the specification and claims herein to "LBP1" includes reference to a fusion polypeptide defining an LBP as defined above.

The terms "analogues" and "derivatives" also extend to any functional chemical equivalent of the LBP characterised by its increased stability and/or efficacy in vivo or vitro. The terms "analogues" and "derivatives" also extend to any amino acid derivative of the LBP as described above.

Analogues of LBP contemplated herein include, but are not limited to, modifications to side chains, incorporation of unnatural amino acids and/or derivatising the molecule and the use of crosslinkers and other methods which impose conformational constraints on the LBP molecule or its analogues. Examples of side chain modifications contemplated by the present invention include modifications of amino groups such as by reductive alkylation by reaction with an aldehyde followed by reduction with $NaBH_4$; amidiation with methylacetimidate; acylation with acetic anhydride; carbamoylation of amino groups with cyanate; trinitrobenzylation of amino groups with 2, 4, 6-trinitrobenzene sulphonic acid (TNBS); acylation of amino groups with succinic anhydride and tetrahydrophthalic anhydride; and pyridoxylation of lysine with pyridoxal-5'-phosphate followed by reduction with $NaBH_4$.

The guanidino group of arginine residues may be modified by the formation of heterocyclic condensation products with reagents such as 2,3- butanedione, phenylglyoxal and glyoxal.

The carboxyl group may be modified by carbodiimide activation via O-acylisourea formation followed by subsequent derivitisation, for example, to a corresponding amide.

Sulphydryl groups may be modified by methods such as carboxymethylation with iodoacetic acid or iodoacetamide;

performic acid lidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate. Other types of modifications include iodination of tyrosine and biotinylation of lysine.

Examples of incorporating unnatural amino acids and derivatives during protein synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy6-methylheptanoic acid, 2-thienyl alanine and/or D-isomers of amino acids.

Crosslinkers can be used, for example, to stabilise 3D conformations, using homo bifunctional crosslinkers such as the bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group-specific reactive moiety such as maleimido or dithio moiety (SH) or carbodiimide (COOH). In addition, peptides could be conformationally constrained by, for example, incorporation of $C_\alpha$ and $N_{60}$-methylamino acids, introduction of double bonds between $C_\alpha$ and $C_\beta$ atoms of amino acids and the formation of cyclic peptides or analogues by introducing covalent bonds such as forming an amide bond between the N and C termini, between two side chains or between a side chain and the N or C terminus.

The LBP molecule of the present invention may also be pegolated using polyethylene glycol (PEG) or other equivalent or similar fatty acid to aid in increasing stability and/or the half life of the protein. In this regard, reference can conveniently be made, for example, to U.S. Pat. No. 5,089,261 which describes the use of PEG to increase the in vivo half life of interleukin 1.

Conveniently, the LBP may be in a purified or semi-purified form from blood, serum or other biological fluid sample. More conveniently, the LBP can be purified or semi-purified by sequential fractionation using affinity chromatography on an immobilised LIF column, anion exchange chromatography, size exclusion chromatography and preparative native polyacrylamide gel electrophoresis. One or more of the foregoing steps may be altered or a similar or equivalent step substituted therefor without departing from the scope of the present invention provided the LBP is enriched from a particular biological sample.

The LIF used in the LIF affinity column is generally of first mammalian origin, i.e. same mammalian or gin for both LBP and LIF although any LIF capable of binding the LBP to be purified can be used in the affinity column.

Conveniently, the purification of the LBP is monitored by binding to labelled LIF and preferably radioactively labelled LIF, such as using known $^{125}$I-LIF binding assays. Other means of monitoring LBP activity can also be used, such as specific antibody binding or inhibition of LIF activity through competitive assays.

The murine LBP (mLBP) in accordance with the preferred aspects of the present invention when purified as generally described above has an apparent molecular weight as determined on SDS-PAGE of approximately 90,000±10,000 daltons in glycosylated form and 65,000±10,000 daltons in another glycosylated form and specifically binds $^{125}$I-murine LIF (mLIF) with an equilibrium dissociation constant of about 0.5–2 nM. Furthermore, mLIF is approximately 1,000–10,000-fold less effective than human LIF (hLIF) in competing with $^{125}$I-hLIF for binding to mLBP. More significantly, however, as shown by the in vitro effects herein described, mLBP is at least 100-fold and is generally about 1,000-fold more active as an inhibitor of hLIF than of mLIF. In addition, the direct binding affinity of mLBP for hLIF is approximately 100 times higher than that for mLIF.

In the most preferred embodiment of the present invention, the mLBP has an amino acid sequence in the N-terminal region comprising Gly-Val-Gln-Asp-Leu-Lys-Cys-Thr-Thr-Asn-Asn-Met-Arg-Val-Trp-Asp-Cys-Thr-Trp-Pro-Ala-Pro -Leu (SEQ ID No. 1), is soluble, particularly in aqueous buffered solutions and has an apparent molecular weight in the glycosylated form of 90,000±10,000 daltons, and preferably 90,000±5,000 daltons as determined by SDS-PAGE. On the basis of treatment with N-glycanase, one deglycosylated form has a molecular weight of approximately 65,000±15,000 daltons and preferably 65,000±10,000 daltons and another deglycosylated form has a molecular weight of approximately 50,000±10,000 daltons as determined by SDS-PAGE. The present invention extends to LBP molecules having an N-terminal amino acid sequence with at least 45%, preferably at least 55%, more preferably at least 65% and still more preferably at least 75–85% and even more preferably greater than 90% similarity to the amino acid sequence: Gly-Val-Gln-Asp-Leu-Lys-Cys-Thr-Thr-Asn-Asn-Met-Arg-Val-Trp-Asp-Cys-Thr-Trp-Pro-Ala-Pro-Leu (SEQ ID No. 1).

The present invention extends to nucleic acid molecules and preferably isolated nucleic acid molecules comprising a sequence of nucleotides encoding or complementary to a sequence encoding an LBP as hereinbefore described including a fusion polypeptide defining an LBP. The nucleotide sequence may correspond to the naturally occurring amino acid sequence of the LBP or may contain single or multiple nucleotide substitutions, deletions and/or additions thereto. Preferably, the nucleic acid encodes an LBP with an N-terminal amino acid sequence comprising Gly-Val-Gln-Asp-Leu-Lys Cys-Thr-Thr-Asn-Asn-Met-Arg-Val-Trp-Asp-Cys-Thr-Trp-Pro-Ala-Pro-Leu (SEQ ID No. 1) or contains a nucleotide sequence capable of hybridising under low, preferably under medium and more preferably under high stringency conditions to a nucleotide sequence encoding the above stated amino acid sequence. Put in alternative terms the hybridising nucleotide sequence is at least 45%, preferably at least 55%, more preferably at least 65–75% and even more preferably greater than 85% similar to the nucleotide sequence encoding the above-stated amino acid sequence.

For the purposes of defining the levels of stringency, reference can conveniently be made to Sambrook et al[15] at pages 387–389 where the washing step at paragraph 11 is considered herein to be high stringency. A low stringency wash is defined herein to be 0.1%–0.5% w/v SDS at 37–45° C. for 2–3 hours and a medium level of stringency is considered herein to be 0.25%–5% w/v SDS at $\geqq 45°$ C. for 2–3 hours. The alternative conditions are applicable depending on concentration, purity and source of nucleic acid molecules.

In a particularly preferred embodiment, the nucleic acid molecule of the present invention is in an expression vector capable of replication and expression in eukaryotic organisms (e.g. CHO cells or other mammalian cells, yeast cells, insects cells) and/or in prokaryotic organisms (e.g. *E. coli*). Such expression vectors and cells transformed with same are convenient sources of the recombinant LBP molecules of the present invention.

The LBP of the present invention will be particularly useful as an inhibitor of the systemic effects of locally produced or administered LIF. Where the use of a heterologous LBP relative to the mammal to be treated is significantly more active than homologous LBP (i.e. LBP from the same species of mammal), then this high activity is particularly advantageous in reducing, for example, the immunological consequences of introducing the heterologous protein into a mammal. The high activity will also enable the administration of as little LBP as possible to ensure that the LBP can be localised to a particular site and cannot disseminate to other areas of the mammal. It may also be important in conjunction with LIF therapy to maintain effective levels of LBP in the circulatory fluids including serum so as to prevent dissemination of LIF administered in the course of the therapy, such as where LIF is locally administered.

Accordingly, another aspect of the present invention contemplates a method of inhibiting the activity of LIF in a mammal comprising administering to said mammal, an effective amount of a soluble LBP.

More particularly, the present invention contemplates a method of inhibiting the activity of LIF in a mammal comprising administering to said mammal, an effective amount of a soluble heterologous LBP wherein said heterologous LBP is capable of greater inhibition of the LIF in the mammal to be treated when compared to a LIF of same mammalian origin to the LBP.

Preferably, the mammal to be treated is a human and the LBP is mLBP.

Preferably, this method is used in the inhibition of the systemic effects of locally produced LIF which are therapeutically undesirable, unintended or unwanted.

Administration may be by any convenient means applicable to the condition being treated but is particularly conveniently administered locally to the site where LIF is to be inhibited. Alternatively, the LBP may be administered to elevate serum levels while LIF is administered locally.

The effective amount of LBP will vary depending on the mammal and condition to be treated but car, range from serum levels of 0.001 $\mu$g/ml to 100 $\mu$g/ml, preferably 0.01 $\mu$g/ml to 50 $\mu$g/ml, more preferably 0.1 $\mu$g/ml to 20 $\mu$g/ml and most preferably 0.5 $\mu$g/ml to 10 $\mu$g/ml. The amount required will be that amount required to completely or partially inhibit LIF activity or at least reduce it to a clinically acceptable level. Furthermore, the "LIF activity" may be all activities associated with LIF or only some of these activities and may be measured in any number of convenient ways such as in a bioassay[9] or a receptor-binding assay.

The LBP may be administered alone or in combination with other active compounds such as, but not limited to, cytokines, antibiotics, anti-cancer agents or immunostimulatory or reducing compounds. Administration of the LBP and other active compounds may be by simultaneous or sequential administration. Furthermore, whether the LBP is administered alone or in combination with other compounds, a single dose of LBP may be sufficient or multiple doses or continuous infusion may be required depending on the condition and mammal to be treated and whether any adverse clinical reactions appear.

Yet a further aspect of the present invention provides a pharmaceutical composition comprising LBP as hereinbefore defined and one or more pharmaceutically acceptable carriers and/or diluents. The preparation of pharmaceutical composition is discussed generally in Remington's Pharmaceutical Sciences, 17th ed. Mach Publishing Co., Easton, Pa., USA. Alternatively, the LBP may be administered genetically using transgenic animal cells or microbial cells.

The active ingredients of the pharmaceutical composition comprising an LBP as herein described are contemplated to exhibit excellent activity when administered in a dosage regimen adjusted to provide the optimum therapeutic response. For example, several divided doses may be administered daily, weekly, monthly or in other suitable time intervals or the dose may be proportionally reduced as indicated by the exigencies of the situation. The active compound may be administered in a convenient manner such as by the oral, topical, intravenous, intramuscular, subcutaneous, intranasal, intradermal or suppository routes or implanting (eg using slow release molecules). Depending on the route of administration, the active ingredient which comprises an LBP may be required to be coated in a material to protect said ingredient from the action of enzymes, acids and other natural conditions which may inactivate said ingredients. In order to administer the vaccine by other than parenteral administration, the LBP may be coated by, or administered with, a material to prevent its inactivation. For example, the LBP may be administered in an adjuvant, co-administered with enzyme inhibitors or in liposomes.

The active compound may also be administered in dispersions prepared in glycerol, liquid polyethylene glycols, and/or mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersion. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thormerosal, and the like. In many cases, it will be preferable to include isotonic agents, for example, sugars or sodium chloride. Prolonged absorption of the injectable compositions can be brought about by, for example, the use in the compositions of agents delaying absorption.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient(s) into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When the LBP is suitably protected as described above, the molecule may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in the vaccine compositions is such that a suitable dosage will be obtained. Preferred compositions or preparations according to the present invention are prepared so that an oral dosage unit form contains between about 0.5 ug and 20 mg of active compound.

The tablets, troches, pills, capsules and the like may also contain the following: a binder such as gum gragacanth, acacia, corn starch or gelatin; excipients such as dicalcium phosphate; a disintegrating agent such as corn starch, potato starch, alginic acid and the like; a lubricant such as magnesium stearate; and a sweetening agent such a sucrose, lactose or saccharin may be added or a flavoring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

As used herein, pharmaceutically acceptable carriers and/or diluents include any and all solvents, dispersion media, aqueous solutions, coatings, antibacterial and antifungal agents, isotonic and absorption delaying agents, and the like. The use of such media and agents for pharmaceutical active substances is well known in the art. Except insofar as any conventional media or agent is incompatible with the active ingredient, use thereof in the composition is contemplated. Supplementary active ingredients can also be incorporated into the compositions.

To reduce the potentially disadvantageous effects of administering a heterologous LBP to a mammal, it may be possible to derivatise or otherwise alter the heterologous LBP to reduce its antigenicity in the mammal to be treated. This can be accomplished by rendering the LBP more like a protein from the mammal to be treated. For example, the LBP can be coupled or masked with a protein or polypeptide or other suitable molecule from the species of mammal to be treated or coupling or fusing the heterologous LBP or parts thereof to the LBP from the target species. In a particularly preferred embodiment, the murine LBP is rendered non-immunogenic in a human and has been derivativatised more like a human molecule.

In yet another aspect of the present invention, the LBP of first mammalian origin is used to detect LIF of second mammalian origin.

In one embodiment, the method contemplated for detecting LIF in a biological sample said method comprising contacting said biological sample with an immobilised LBP from a mammal wherein the LBP is capable of inhibiting the ability of the first mentioned LIF to induce differentiation of M1 myeloid leukaemic cells in vitro to a greater extent when compared to its ability to inhibit LIF of same mammalian origin as LBP and/or wherein said LBP has at least a 100-fold higher binding affinity for said first mentioned LIF compared to the binding affinity of LIF of same mammalian origin as said LBP wherein said contact is for a time and under conditions sufficient for a complex to form between the immobilised LBP and the LIF in the sample; contacting the LBP-LIF complex with an antibody specific for said LIF and labelled with a reporter molecule capable of providing a signal; determining the presence of bound LIF on the basis of the signal produced by said reporter molecule.

In an alternative embodiment, the LBP-LIF complex is contacted with an unlabelled antibody specific to said LIF and then LIF is detected by a second antibody labelled with a reporter molecule and specific to said first antibody.

In yet another alternative embodiment, the LIF in the sample is immobilised (e.g. by an immobilised antibiody) and then bound LIF detected by labelled LBP or first by unlabelled LBP followed by a labelled antibody specific to said LBP.

An embodiment of this aspect of the present invention is described hereinafter with reference to the preferred embodiment of using mLBP to detect hLIF. The present invention, however, is not so limited and extends to the use of LBP and LIF from other mammals.

According to this embodiment, there is contemplated a method of detecting hLIF in a biological sample, said method comprising contacting said sample to mLBP as hereinbefore defined, immobilised to a solid support for a time and under conditions sufficient for a mLBP-hLIF complex to form and then detecting for the presence of said mLBP-hLIF complex.

In a particularly preferred method, the mLBP-hLIF complex is detected by contacting the complex with an antibody for hLIF with the antibody itself being labelled with a reporter molecule or with an additional step of contacting the mLBP-hLIF-antibody complex with a labelled second antibody capable of binding to the first antibody.

The antibodies may be polyclonal or monoclonal and both are obtainable by immunization of a suitable animal with hLIF and either type is utilizable in the LIF assay. The methods of obtaining both types of sera are well known in the art. Polyclonal sera are less preferred but are relatively easily prepared by injection of a suitable laboratory animal with an effective amount of hLIF, or antigenic parts thereof, collecting serum from the animal, and isolating specific sera by any of the known immunoadsorbent techniques. Although antibodies produced by this method are utilizable in virtually any type of LIF assay, they are generally less favoured because of the potential heterogeneity of the product.

The use of monoclonal antibodies in an immunoassay is particularly preferred because of the ability to produce them in large quantities and the homogeneity of the product. The preparation of hybridoma cell lines for monoclonal antibody production derived by fusing an immortal cell line and lymphocytes sensitized against the immunogenic preparation can be done by techniques which are well known to those who are skilled in the art. (See, for example Douillard and Hoffman, Basic Facts about Hybridomas, in *Compendium of Immunology* Vol II, ed. by Schwartz, 1981; Kohler and Milstein, *Nature* 256: 495–499, 1975; *European Journal of Immunology* 6: 511–519, 1976).

The presence of a hLIF may be accomplished in a number of ways such as by Western blotting and ELISA procedures. A wide range of immunoassay techniques are available as can be seen by reference to U.S. Pat. Nos. 4,016,043, 4,424,279 and 4,018,653. These, of course, include both single-site and two-site or "sandwich" assays of the non-competitive types, as well as in the traditional competitive binding assays. These assays also include direct binding of a labelled antibody to a target.

Sandwich assays are among the most useful and commonly used assays and are favoured for use in the present invention. A number of variations of the sandwich assay technique exist, and all are intended to be encompassed by the present invention. Briefly, in a typical forward assay, mLBP is immobilized on a solid substrate and the sample to be tested brought into contact with the bound molecule. After a suitable period of incubation, for a period of time sufficient to allow formation of an mLBP-hLIF complex, an antibody specific to the hLIF, labelled with a reporter molecule capable of producing a detectable signal, is then added and incubated allowing sufficient time for the formation of a complex of mLBP-hLIF-labelled antibody. Any unreacted material is washed away, and the presence of the hLIF is determined by observation of a signal produced by the reporter molecule. The results may either be qualitative, by simple observation of the visible signal, or may be quantitated by comparing with a control sample containing known amounts of hapten. Variations on the forward assay include a simultaneous assay, in which both sample and labelled antibody are added simultaneously to the bound mLBP. In accordance with the present invention the sample is one which might contain hLIF and includes biological fluid (e.g. blood, serum, tissue extract) fermentation fluid and supernatant fluid such as from a cell culture.

In the typical forward sandwich assay, mLBP or a hLIF-binding part thereof is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, discs of microplates, or any other surface suitable for conducting an immunoassay. The binding processes are well-known in the art and generally consist of cross-linking covalently binding or physically adsorbing mLBP to the polymer. After immobilising the mLBP, the polymer-mLBP complex is washed in preparation for the test sample. An aliquot of the sample to be tested is then added to the solid phase complex and incubated for a period of time sufficient (e.g. 2–40 minutes) and under suitable conditions (e.g. 25° C.) to allow binding of hLIF in the sample to the immobilised mLBP. Following the incubation period, the complex is washed and optionally dried and then incubated with an antibody specific for hLIF. The antibody is linked to a reporter molecule which is used to indicate the binding of hLIF to mLBP. Alternatively, a second antibody conjugated to a reporter molecule and capable of binding to the first antibody may be used.

An alternative method involves immobilizing the target molecules (i.e. hLIF) in the biological sample and then exposing the immobilized target to mLBP which may or may not be labelled with a reporter molecule. Depending on the amount of target and the strength of the reporter molecule signal, a bound target may be detectable by direct labelling of mLBP. Alternatively, a labelled antibody, specific to mLBP is exposed to the complex to form a tertiary complex. The complex is detected by the signal emitted by the reporter molecule.

By "reporter molecule" as used in the present specification, is meant a molecule which, by its chemical nature, provides an analytically identifiable signal which allows the detection of antigen-bound antibody. Detection may be either qualitative or quantitative. The most commonly used reporter molecules in this type of assay are either enzymes, fluorophores or radionuclide containing molecules (i.e. radioisotopes) and chemiluminescent molecules.

In the case of an enzyme immunoassay, an enzyme is conjugated to the hLIF-specific antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, beta-galactosidase and alkaline phosphatase, amongst others. The substrates to be used with the specific enzymes are generally chosen for the production, upon hydrolysis by the corresponding enzyme, of a detectable color change. Examples of suitable enzymes include alkaline phosphatase and peroxidase. It is also possible to employ fluorogenic substrates, which yield a fluorescent product rather than the chromogenic substrates noted above. Generally, the enzyme-labelled antibody is added to the mLBP-hLIF complex, allowed to bind, and then the excess reagent is washed away. A solution containing the appropriate substrate is then added to the tertiary complex. The substrate will react with the enzyme linked to the antibody, giving a qualitative visual signal, which may be further quantitated, usually spectrophotometrically, to give an indication of the amount of hapten which was present in the sample. "Reporter molecule" also extends to use of cell agglutination or inhibition of agglutination such as red blood cells on latex beads, and the like.

Alternately, fluorescent compounds, such as fluorecein and rhodamine, may be chemically coupled to antibodies without altering their binding capacity. When activated by illumination with light of a particular wavelength, the fluorochrome-labelled antibody adsorbs the light energy, inducing a state to excitability in the molecule, followed by emission of the light at a characteristic color visually detectable with a light microscope. As in the EIA, the fluorescent labelled antibody is allowed to bind to the mLBP-hLIF. After washing off the unbound reagent, the tertiary complex is then exposed to the light of the appropriate wavelength and the fluorescence observed indicates the presence of the hapten of interest. Immunofluoresence and EIA techniques are both very well established in the art and are particularly preferred for the present method. However, other reporter molecules, such as radioisotope, chemiluminescent or bioluiminescent molecules, may also be employed. The above considerations apply where the antibody is an anti-immunoglobulin and is labelled so that a quaternay complex is obtained.

Furthermore, the mLBP of the present invention may be packaged in kit form, for example, to conduct an assay for LIF. The kit is in compartmental form adapted to contain mLBP and may further comprise in the same or different compartments the reagents for the LIF assay.

The foregoing description is equally applicable to the use of LBP from a first mammalian species to detect LIF from a second mammalian species as hereinbefore defined. Furthermore, variations such as binding LIF using immobilised antibodies and then detecting the bound LIF with LBP conjugated to a reporter molecule or using first LBP then LBP-binding antibody conjugated to a reporter molecule.

The present invention is further described by reference to the following non-limiting Figures and/or Example.

In the Figures:

FIGS. 1A–1B is a graphical representation showing size exclusion profile of $^{125}$I-mLIF in the presence and absence of normal mouse serum. The Ultrogel AcA44 (20×1 cm) column was equilibrated and run in 20 mM Na phosphate buffer pH 7.4, 150 mM NaCl (PBS) at 0.2 ml/min, collecting 1 min fractions that were counted in a gamma counter. (A) 100,000 cpm $^{125}$I-mLIF in 100 µl PBS (B) 100,000 cpm $^{125}$I-mLIF preincubated with 100 µl normal mouse serum for 16 hr at room temperature.

FIGS. 2A–2C are graphical representation showing representative fractionations of normal mouse serum by LIF affinity chromatography, anion exchange chromatography and size exclusion chromatography. Absorbance and specific $^{125}$I-mLIF binding of fractions in a Con-A Sepharose binding assay are shown. (A) 50 ml mouse serum was applied to a column of LIF-pABAE-Sepharose 4B in PBS and eluted with guanidine-HCl as described in the Example. (B) Active fractions from affinity chromatography were pooled, applied to a Mono-Q HR 5/5 and eluted with a salt gradient as described in the Example. (C) Active fractions from anion-exchange chromatography were pooled, concentrated to 100 µl and injected onto a Superose-12 10/30 column equilibrated in PBS, and elution was carried out isocratically using the same buffer.

FIGS. 3A–3B is a photographic and graphical representation of preparative native gel electrophoresis of LBP. Upper panel (A): Fractions from size-exclusion chromatography containing LIF-binding activity were pooled and applied to a 20 ml 7.5% w/v polyacrylamide native gel and electrophoresed in a BioRad Model 491 Prep Cell as described in the Example. Specific $^{125}$I-mLIF binding of eluted fractions in a Con-A Sepharose binding assay is shown. Lower panel (B): NaDodSO$_4$-PAGE of 20 µl aliquots of pooled fractions containing LBP activity from various stages of purification: s, low molecular weight standards (Pharmacia) (MW×10$^{-3}$); a, normal mouse serum (1/50); b & c, 1$^{st}$ LIF-pABAE Sepharose 4B column; d, 2$^{nd}$ LIF-pABAE Sepharose 4B column; e, Mono-Q HR 5/5 column; f, Superose-12 10/30 column; g, preparative native gel electrophoresis, arrow shows band of interest.

FIGS. 4A–4C is a graphical representation showing Scatchard analysis of $^{125}$I-mLIF binding to LBP, solubilized murine liver membranes and 3T3-L1 cells. (A) Saturation isotherm for $^{125}$I-mLIF binding to mouse serum (5 µl in 210 µl total) showing total cpm bound (▲), non-specific cpm bound (●) and specific cpm bound (○). (B) Scatchard transformation of $^{125}$I-mLIF binding to LBP in mouse serum (5 µl in 210 µl total) (○) and purified LBP (1 µl in 90 µl total) (●). (C) Scatchard transformation of $^{125}$I-mLIF binding to solubilized murine liver membranes (25 µl in 175 µl total) (○) and 3T3-L1 cells (0.6×10$^6$ in 80 µl total) (●).

Figure 6A:
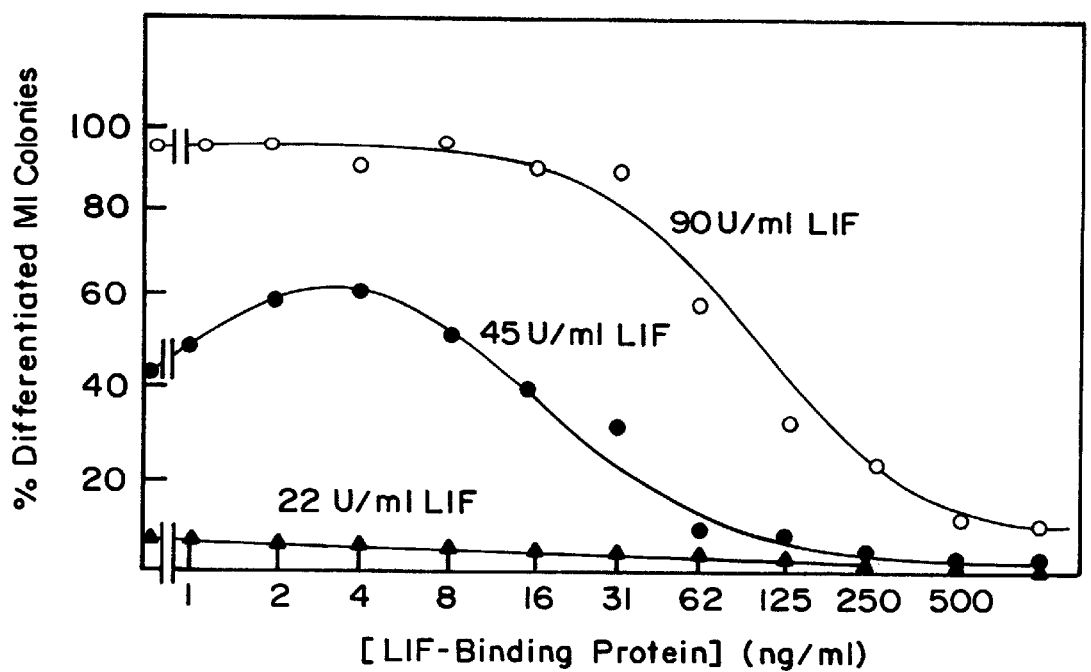
FIGS. 6A–6B is a graphical representation showing blocking of induction of differentiation of mLIF stimulated colonies of M1 leukemic cells by affinity-purified LBP. (A) Titration of LBP in the presence of constant amounts of mLIF as indicated. (B) Titration of mLIF with constant levels of LBP as indicated.
Figure 7A:
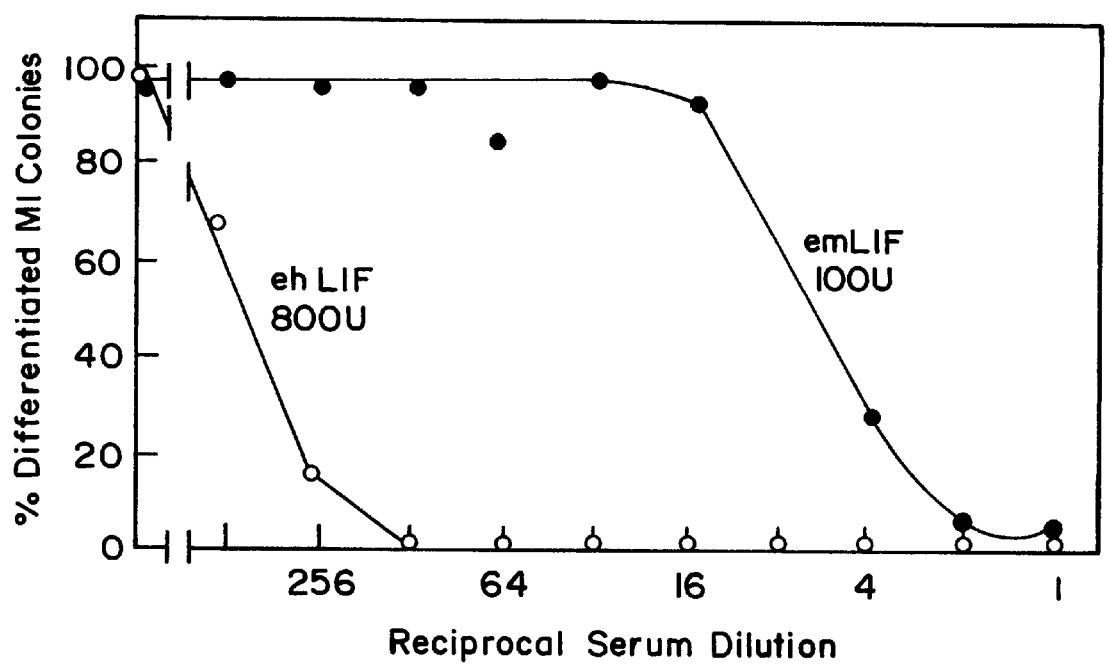
Figure 7B:
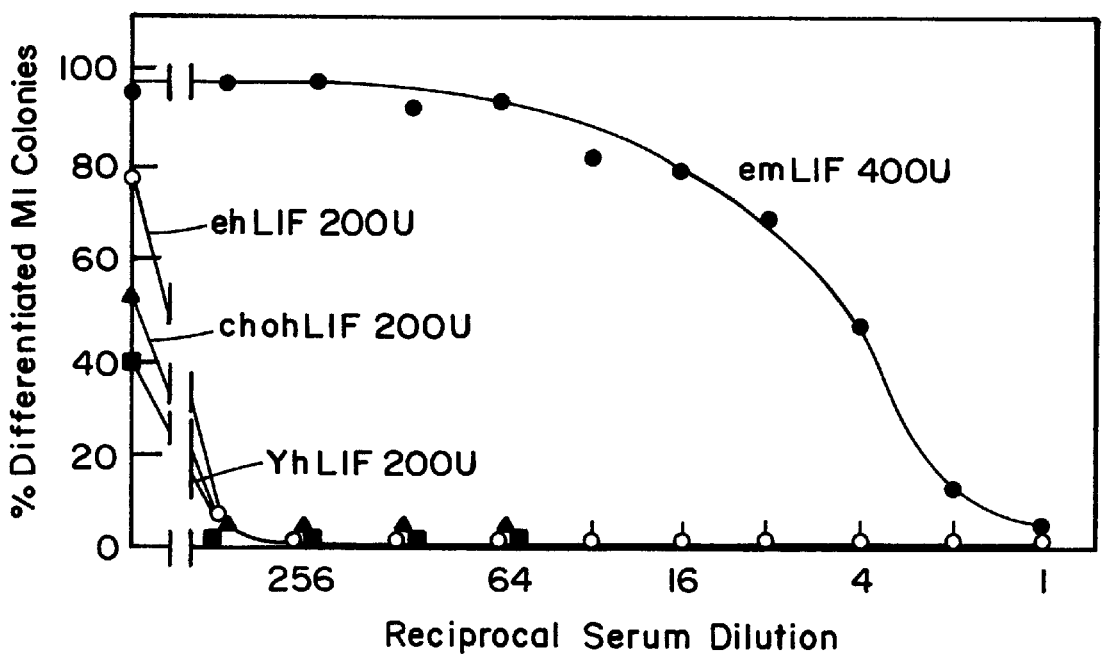

FIGS. 7A–7B is a graphical representation showing the blocking of induction of mLIF and hLIF stimulated colonies of M1 leukaemic cells by normal mouse serum. mLIF and hLIF have an equal ability to stimulate the differentiation of murine M1 colonies. A. Effect on 100 U *E. coli* derived murine LIF (emLIF) and 800 U *E coli* derived human LIF (ehLIF). B. Effect on 400 U emLIF and 200 U each of ehLIF, CHO cells derived human LIF (chohLIF) and yeast derived human LIF (YhLIF). As in FIG. 6A, a 1:8 dilution of normal mouse serum (equivalent to 125 ng/ml LBP) was able to inhibit 50% of activity stimulated by 100 U/ml mLIF. In contrast, as little as 1:512 dilution of normal mouse serum (equivalent to –1.5 ng/ml LBP) was able to inhibit 50% of the activity stimulated by 800 U/ml hLIF.

Figure 8A:
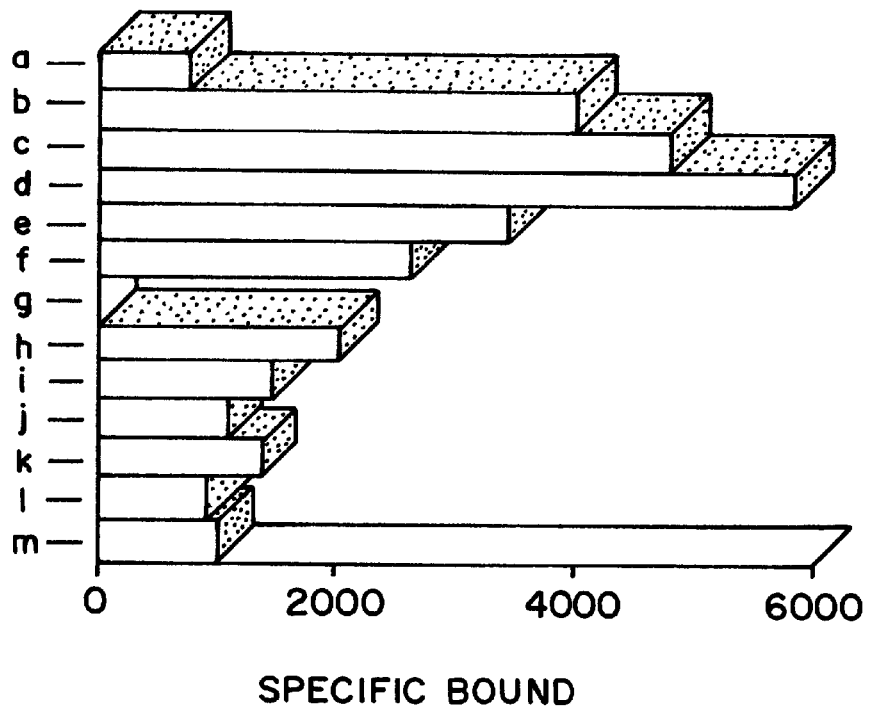
Figure 8B:
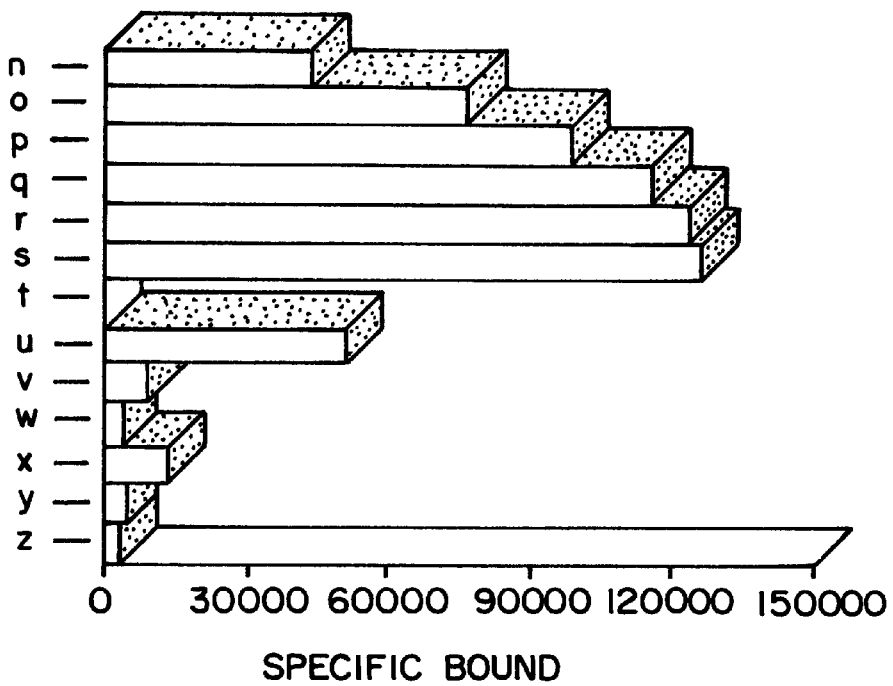
Figure 9:
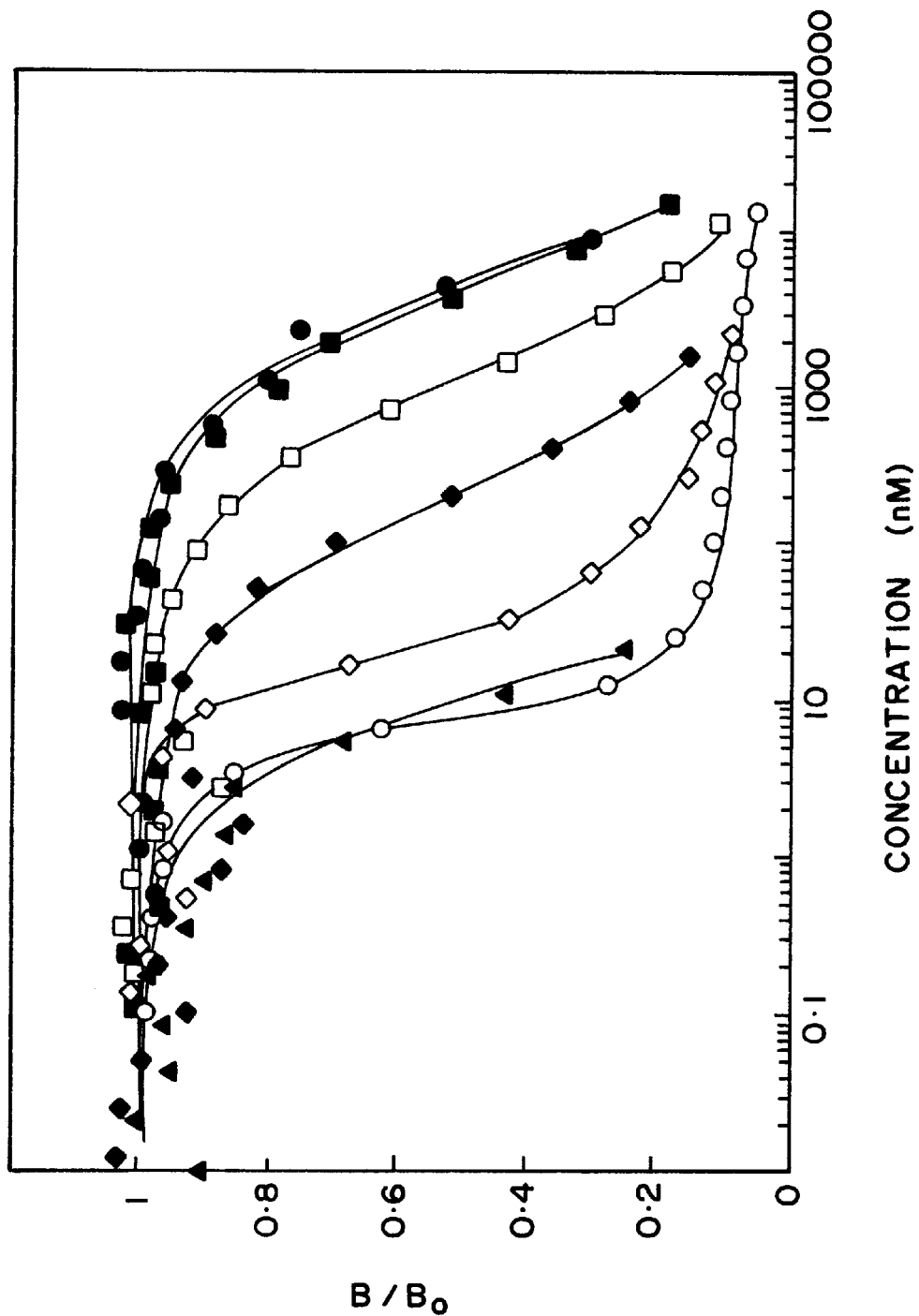

FIGS. 8A–B is a graphical representation showing specific binding of $^{125}$I-mLIF (A) and $^{125}$I-hLIF (B) to mLBP immobilized onto 96-well PVC plates. Affinity purified mLBP was diluted in various buffers (PBS, 0.1M NaHCO$_3$ pH9.5 and 0.1M NaHCO$_3$ pH9.5 containing 4 µg/ml bovine serum albumin (BSA)) and 100 µl aliquots incubated in 96-well PVC plates (Costar) for 16 hours at room temperature. The plates were then washed with PBS containing 0.05% v/v Tween-20 (wash buffer) and blocked with Hepes-buffered RPMI medium containing 10% v/v Foetal calf serum (HRF) for 1 hour at room temperature. The plates were again washed with wash buffer then incubated with 50 µl HRF containing $^{125}$I-mLIF or $^{125}$I-hLIF for 16 hours at room temperature. Non-specific binding was determined from incubations containing in addition 20 µl of 50 µg/ml unlabelled mLIF or hLIF. Bound and free labelled ligand were separated by washing the plates three times in wash buffer. The plates were dried and the assay plates containing the bound labelled ligand were exposed to a phosphorimager screen (Molecular Dynamics) for 24 hours. Results were analysed using Imagequant version 3 (Molecular Dynamics) software. The alphabetically labelled bars are as follows:

a) 5.76 µg/ml mLBP in PBS
b) 2.88 µg/ml mLBP in 0.1M Na bicarbonate pH9.5
c) 1.44 µg/ml mLBP in 0.1M Na bicarbonate pH9.5
d) 0.72 µg/ml mLBP in 0.1M Na bicarbonate pH9.5
e) 0.36 µg/ml mLBP in 0.1M Na bicarbonate pH9.5
f) 0.18 µg/ml mLBP in 0.1M Na bicarbonate pH9.5
g) 5.76 µg/ml mLBP in PBS+4 µg/ml BSA
h) 2.88 µg/ml mLBP in 0.1M Na bicarbonate pH9.5+4 µg/ml BSA
i) 1.44 µg/ml mLBP in 0.1M Na bicarbonate pH9.5+4 µg/ml BSA
j) 0.72 µg/ml mLBP in 0.1M Na bicarbonate pH9.5+4 µg/ml BSA
k) 0.36 µg/ml mLBP in 0.1M Na bicarbonate pH9.5+4 µg/ml BSA
l) 0.18 µg/ml mLBP in 0.1M Na bicarbonate pH9.5+4 µg/ml BSA
m) 5.76 µg/ml mLBP in PBS
n) 2.88 µg/ml mLBP in 0.1M Na bicarbonate pH9.5
o) 1.44 µg/ml mLBP in 0.1M Na bicarbonate pH9.5
p) 0.72 µg/ml mLBP in 0.1M Na bicarbonate pH9.5
q) 0.36 µg/ml mLBP in 0.1M Na bicarbonate pH9.5
r) 0.18 µg/ml mLBP in 0.1M Na bicarbonate pH9.5
s) 5.76 µg/ml mLBP in PBS+4 µg/ml BSA t) 2.88 µg/ml mLBP in 0.1M Na Bicarbonate pH9.5+4 µg/ml BSA u) 1.44 µg/ml mLBP in 0.1M Na Bicarbonate pH9.5+4 µg/ml BSA v) 0.72 µg/ml mLBP in 0.1M Na Bicarbonate pH9.5+4 µg/ml BSA w) 0.36 µg/ml mLBP in 0.1M Na Bicarbonate pH9.5+4 µg/ml BSA x) 0.18 µg/ml mLBP in 0.1M Na Bicarbonate pH9.5+4 µg/ml BSA FIG. 9 is a graphical representation showing competitive binding of mouse LIF (●) human LIF (○), porcine LIF (▲) and a series of mouse-human LIF chimeric molecules (■, □, ◆, ◇) Aliquots of 20 µl of normal mouse serum diluted 1 in 20 in PBS were added to 96-well filtration assay plates containing a 0.65 micron Durapore membrane (Millipore) with 10 µl $^{125}$I-hLIF, 50 µl unlabelled ligand diluted in PBS and 25 µl Concanavalin-A Sepharose 4B (diluted 1 in 4 in 0.1M sodium acetate pH6.0 containing 1 mM each $MgCl_2$, $MnCl_2$ and $CaCl_2$) and incubated at room temperature, overnight, with agitation. Bound and free radioactivity were separated by vacuum filtration of the supernatant, and the Concanavalin-A Sepharose pellet was washed once with cold PBS. Assay plates containing the Concanavalin-A Separose pellet were exposed to a phosphorimager screen (Molecular Dynamics) for 24 hours. Results were analysed using Imagequant version 3 (Molecular Dynamics) software.

Figure 10A:
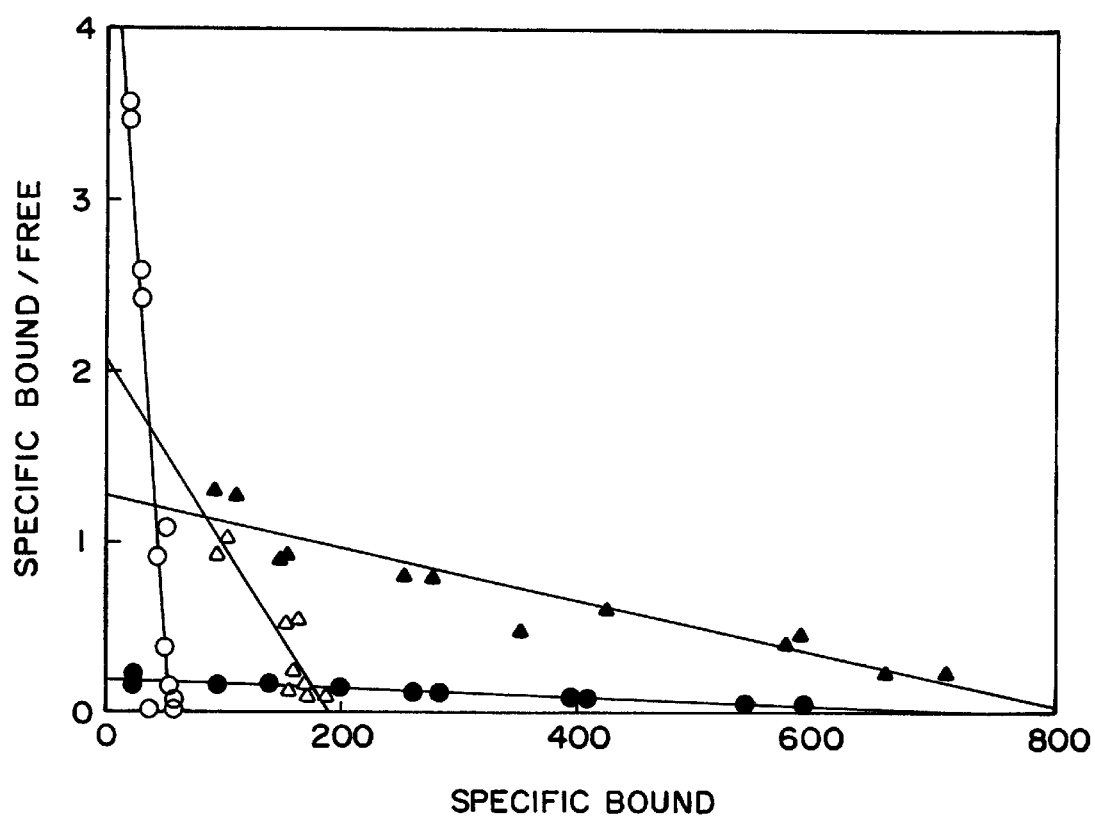
Figure 10B:
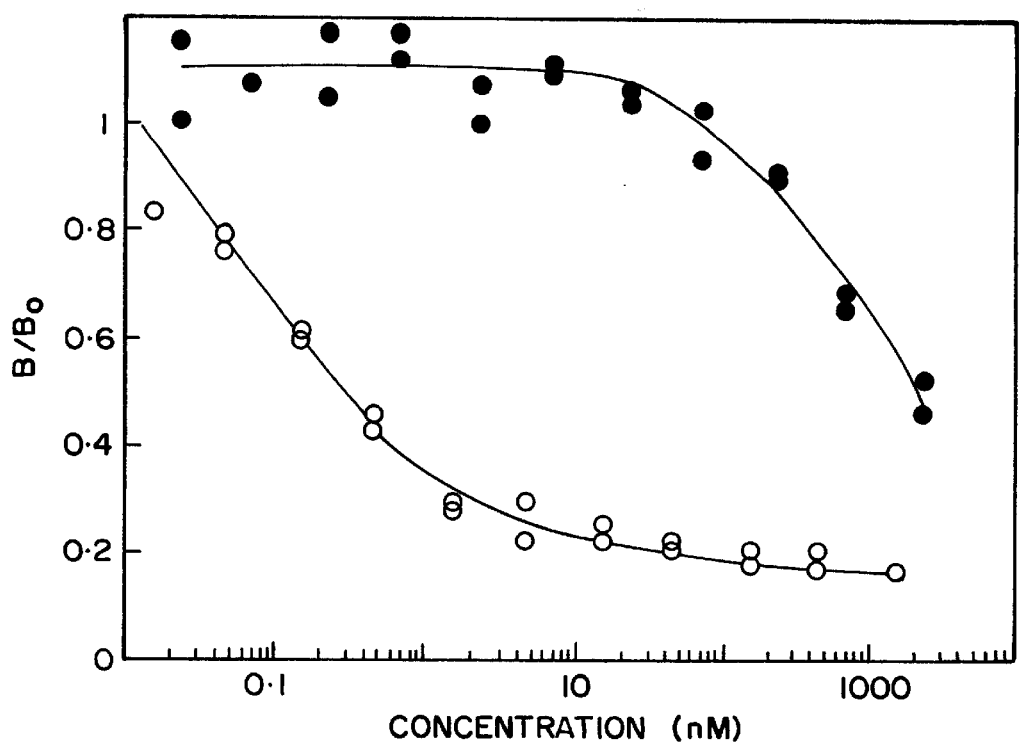
Figure 10C:
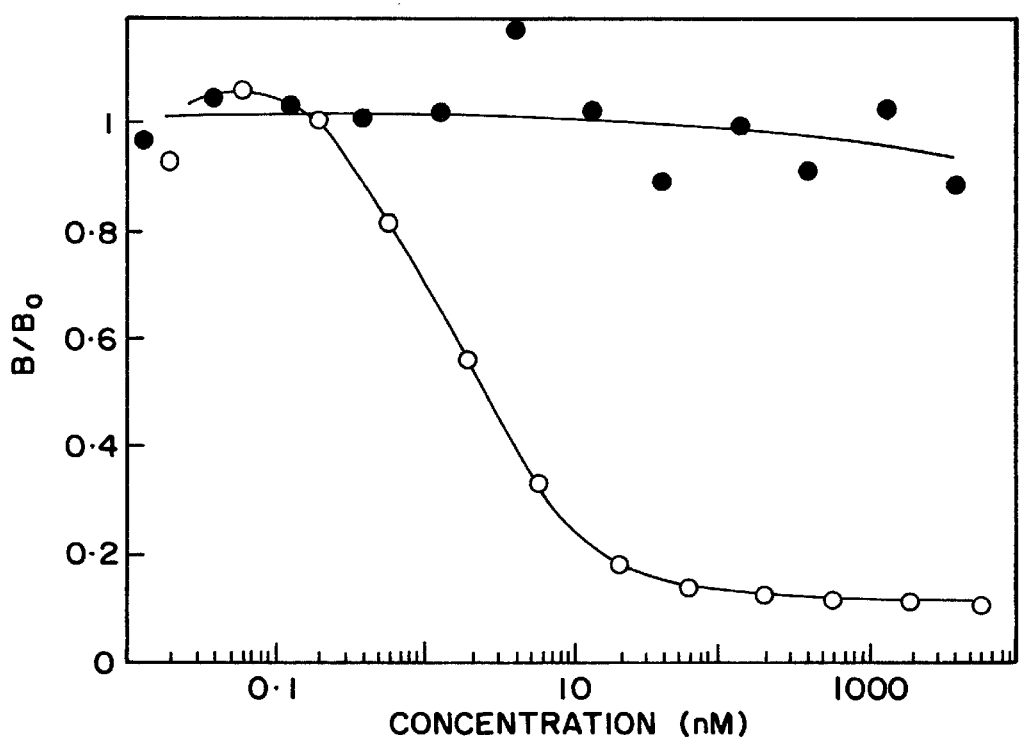

FIG. 10A–C is a graphical representation showing comparative binding data for mLIF and hLIF to mLBP and recombinant hLIF receptor α-chain.

(A) Scatchard analysis of $^{125}$I-mLIF binding to mLBP (normal mouse serum diluted 1 in 20) (●, $K_d$=1–4 nM), $^{125}$I-hLIF binding to mLBP (normal mouse serum diluted 1 in 1000) (○, $K_d$=17 pM), $^{125}$I-hLIF binding to conditioned medium collected 4 days after transfection of COS cells with a plasmid encoding a soluble truncated form of the hLIF receptor α-chain (▲, $K_d$≈300–400 pM) and $^{125}$I-hLIF binding to 44×10$^6$ cells/ml Allen1 cells, which express a high affinity hLIF receptor (Δ, $K_d$=80 pM).

Figure 5A:
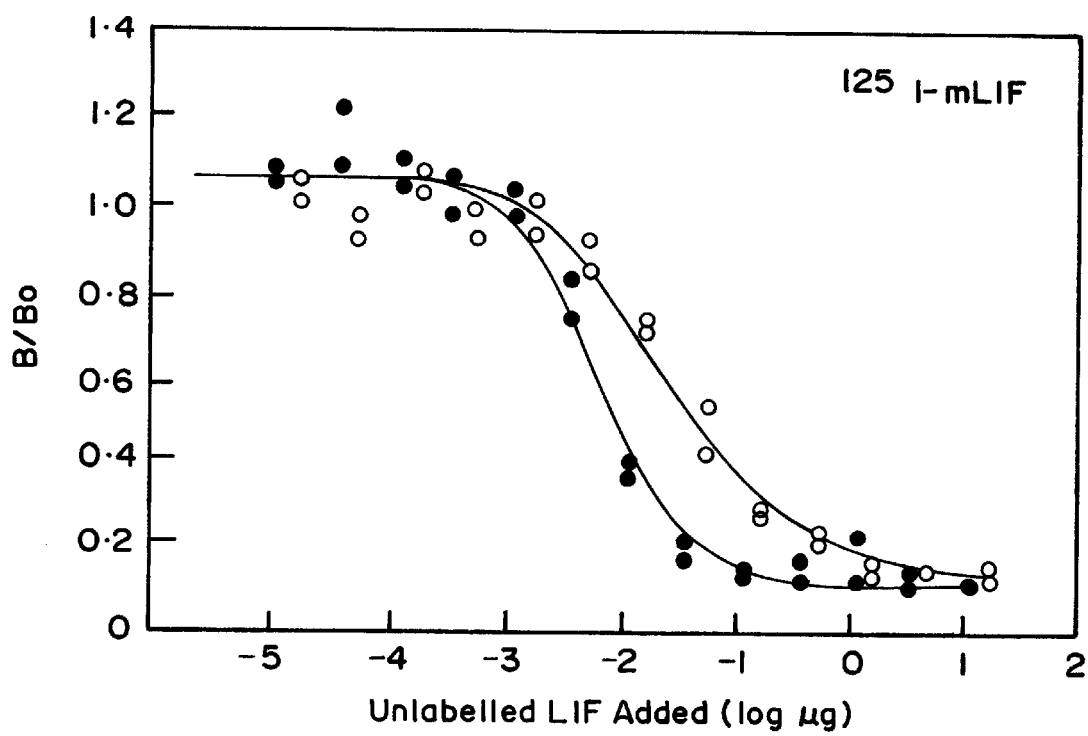
FIGS. 5A–5B is a graphical representation of displacement curves for unlabelled mLIF (○) and hLIF (●) competing with the binding of (A) $^{125}$I-mLIF and (B) $^{125}$I-hLIF for purified LBP (100 µl total volume).

(B) Competition of unlabelled mouse LIF (●, $ID_{50}$=500 nM) and human LIF (○, $ID_{50}$=0.1 nM) with $^{125}$I-hLIF for binding to mLBP. Experimental conditions were as described in FIG. 5.

(C) Competition of unlabelled mouse LIF (●, $ID_{50}$>10,000 nM) and human LIF (○, $ID_{50}$=2 nM) with $^{125}$I-hLIF for binding to conditioned medium collected 4 days after transfection of COS cells with a plasmid encoding a soluble truncated form of the hLIF receptor α-chain. Experimental conditions were as described in FIG. 5.

FIG. 11A is a photographic representation showing Coomassie Blue stained gel of elution fractions from hLIF-Affigel-10 column. The hLIF-Affigel column was synthesized using 5 ml Affigel-10 (BioRad), 3.5 mg hLIF and 5 mg ovalbumin as a filler protein according to manufacturer's instructions. An amount of 60 ml of normal $C_3$H/HeJ mouse serum (as a source of mLBP) was applied to the 5 ml hLIF-Affigel-10 column equilibrated in PBS. The column was eluted with 85 ml equilibration buffer and a 30 ml linear gradient to 6M guanidine-HCl in the same buffer. Fractions of 2.5 ml were collected throughout at a flow rate of 0.5 ml/min, exchanged where necessary into equilibration buffer using PD10 columns (Pharmacia) and concentrated to 1 ml using Centricon microconcentrators (Amicon). SDS-PAGE was performed according to the method of Laemmli[(4)]. Aliquots of 15 µl of each fraction were diluted 1 in 2 in SDS sample buffer and electrophoresed in 13% w/v polyacrylamide gels in a Mini-Protean II system (BioRad) and stained with Coomassie Brilliant Blue. The positions of the molecular weight markers are shown.

Figure 11B:
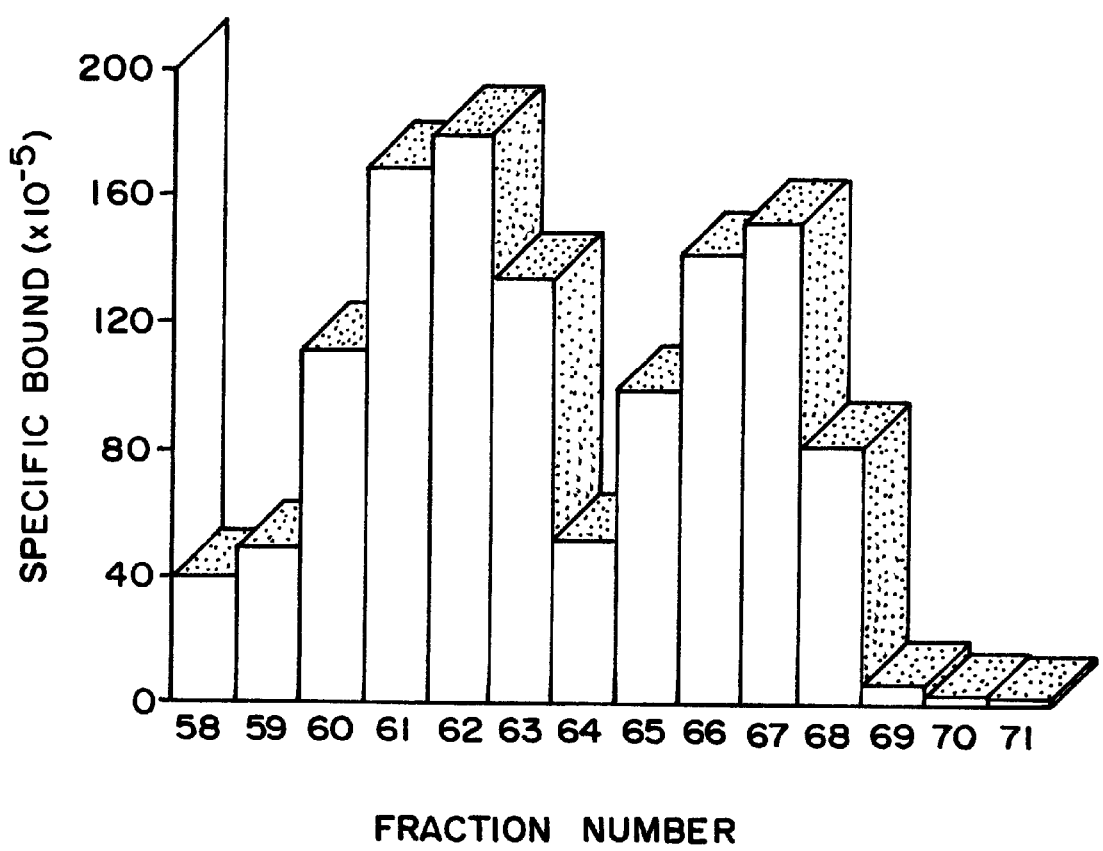

FIG. 11B is a graphical representation showing monitoring of mLBP amounts by direct $^{125}$I-mLIF binding assays of elution fractions from hLIF-Affigel-10 column.

Figure 12:
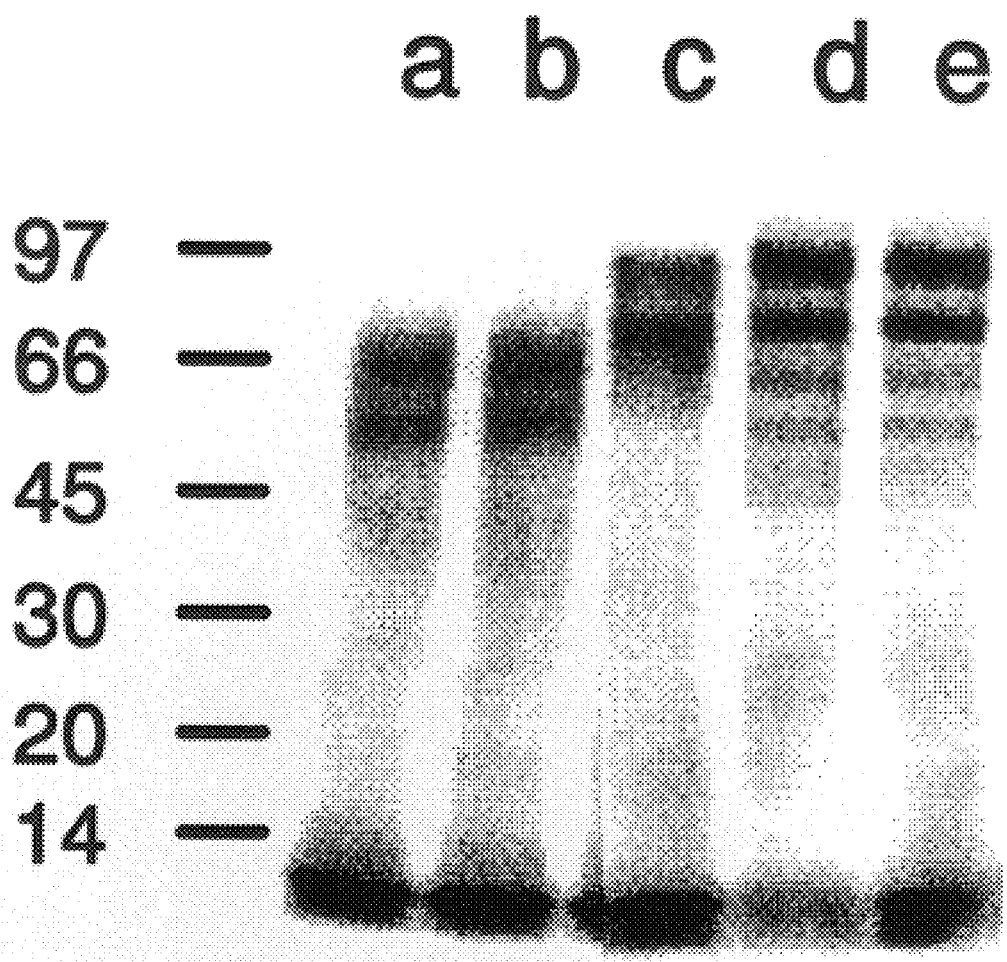

FIG. 12 is a photographic representation showing deglycosylation of mLBP using N-glycanase. Aliquots of $^{125}$I-mLBP in 50 mM sodium phosphate pH7.5 were incubated in the presence of 0.25 units of N-glycanase (Genzyme) in the same buffer (lanes a and b), buffer alone (lane c) or 0.25 units of N-glycanase, 0.1% w/v SDS and 1% v/v 2-mercaptoethanol in the same buffer (lanes d and e) at 37° C. for 24 hours. The incubation mixtures were diluted 1 in 2 in SDS sample buffer and electrophoresed in 10% w/v polyacrylamide gels in a Mini-Protean II system (BioRad), stained with Coomassie Brilliant Blue, dried and exposed to a phosphorimager screen (Molecular Dynamics) for 24 hours. Results were analysed using Imagequant version 3 (molecular Dynamics) software. The positions of the molecular weight markers are shown.

EXAMPLE 1

1. Materials and Methods

Collection of Mouse Sera

Blood from C57BL/6J, C3H/HeJ, CBA f/Ca H, DBA/2J and BALB/C/An Bradley mice was collected by exsanguination. Red cells were separated from the serum by centrifugation at 3000 g for 10 min, and the serum stored at −20° C. for up to 6 months.

Affinity Chromatography

Leukaemia Inhibitory Factor p-aminobenzamidoethyl-Sepharose 4B (LIF-pABAE Sepharose 4B) was prepared according to the method of Cuatrecasas and Anfinsen[2]. Briefly, 8.4 g CNBr-Activated Sepharose 4B (Pharmacia, Uppsala) was washed in 1 mM HCl, reacted with an equal volume of 2M ethylene diamine at pH10 for 16 hr at 4° C. The p-nitrobenzamido-ethyl Sepharose 4B was washed extensively with 50% v/v dimethyl formamide, then reduced with 0.2M sodium dithionite in 0.5M sodium bicarbonate pH8.5 for 60 min. at 40° C. The p-aminobenzamidoethyl Sepharose 4B was washed in 0.5M HCl then diazotised with 0.1M sodium nitrite for 7 min at 4° C. Aliquots of 7 ml of this diazonium-Sepharose derivative were then reacted with 8 mg each of E. coli-derived murine LIF[3] and chicken ovalbumin (Sigma, MO) as a non-specific filler protein in 10 ml 0.2M sodium tetraborate pH9.2 for 16 hr at 4° C. The LIF-pABAE-Sepharose 4B was washed extensively with 20 mM sodium phosphate pH7.4 containing 150 mM sodium chloride (PBS) and 6M guanidine-HCl in PBS before use.

Aliquots of 50 ml mouse serum or pooled fractions containing LIF-binding protein (LBP) activity in PBS were applied to a 13×0.7 cm column of LIF-pABAE-Sepharose 4B equilibrated in PBS (this and all succeeding buffers contained 0.02% v/v Tween 20 and 0.02% w/v sodium azide) and eluted with 20 ml equilibration buffer followed by a 15 ml linear gradient to 6M guanidine-HCl in the same buffer. Fractions of 2.5 ml were collected at a flow rate of 0.5 ml/min and exchanged where necessary into equilibration buffer using a prepacked Sephadex G-25 column (PD10, Pharmacia, Uppsala).

Anion-exchange Chromatography

Fractions from affinity chromatography containing LIF-binding activity were pooled and diluted 20-fold with 20 mM Tris pH7.0, then applied to a Mono-Q HR 5/5 (Pharmacia, Uppsala) column equilibrated in the same buffer. Elution was carried out using 25 ml of equilibration buffer, followed by a 30 ml linear gradient to 1M NaCl in equilibration buffer. The 0.5 ml fractions were collected at a flow rate of 0.5 ml/min.

Size-exclusion Chromatography

Fractions from anion-exchange chromatography containing LIF-binding activity were pooled and concentrated to 100 µl using a Centricon-10 microconcentrator (Amicon, MA). The sample was injected onto a Superose-12 10/30 (Pharmacia, Uppsala) column equilibrated in PBS, and elution was carried out isocratically using the same buffer. The 0.2 ml fractions were collected at a flow rate of 0.2 ml/min.

Preparative Native Polyacrylamide Gel Electrophoresis

Fractions from size-exclusion chromatography containing LIF-binding activity were diluted 2-fold in 0.062M Tris pH6.8, 12.5% v/v glycerol, 0.02% w/v bromophenol blue, applied to a 20 ml 0.375M Tris pH8.8, 7.5% w/v polyacrylamide/0.2% w/v Bis separating gel with a 10 ml 0.125M Tris pH6.8, 4% w/v acrylamide/0.11% w/v stacking gel, containing no sodium dodecyl sulfate (NaDodSO$_4$). The sample was electrophoresed in a Model 491 Prep Cell (BioRad, CA) using a 0.025M Tris, 0.19M glycine buffer pH8.3 as an electrode buffer at 40 mA for approximately 6 hr. Fractions of 2.5 ml were collected at a flow rate of 1 ml/min after the elution of the bromophenol blue dye front from the gel.

Analytical Sodium Dodecyl Sulfate Polyacrylamide Gel Eelectrophoresis

NaDodSO$_4$-PAGE was performed according to the method of Laemmli[4]. Aliquots of samples to be analysed were diluted in NaDodSO$_4$ sample buffer and electrophoresed in 12.5% w/v polyacrylamide gels in a Mini-Protean II system (BioRad, CA) and silver-stained[5].

Iodination of LIF

Amounts of 1–2 µg recombinant murine or human LIF produced in *E. coli* were iodinated and purified as previously described[(3)]. The iodinated materials retained biological activity and had specific activities of 3–5×10$^5$ cpm/pmole for $^{125}$I-mLIF and 6–10×10$^5$ cpm/pmole for $^{125}$I-hLIF.

Binding Assays

Aliquots of samples containing the LIF-binding activity were added to Eppendorf tubes containing 10 µl $^{125}$I-LIF (5–10×10$^4$ cpm) and 50–100 µl concanavalin-A Sepharose (Pharmacia, Uppsala) (diluted four-fold in 100 mM sodium acetate pH6.0 containing 1 mM each MgCl$_2$, MnCl$_2$ and CaCl$_2$). Non-specific binding was determined from incubations containing in addition 10 µl of 50 µg/ml unlabelled LIF. Assay tubes were incubated at room temperature for 16 hr with agitation. Bound and free label were separated by resuspending the incubation mixture, layering it over 150 µl fetal calf serum (FCS) in a tapered microcentrifuge tube and spinning at 13,000 rpm for 1 min. The tip of the tube, containing the Sepharose pellet, was then cut off using a scalpel blade and both the pellet and supernatant were counted for 1 min in a gamma counter (Packard Crystal Multidetector, Packard Instruments).

For competitive binding experiments, LBP and Concanavalin-A Sepharose were incubated with between 1×10$^{-4}$ and 2×10$^4$ ng unlabelled ligand and a fixed concentration (2 nM) of labelled ligand and then processed as described above.

Scatchard Analyses

3T3-L1 cells were maintained as previously described[6] and harvested using Hepes buffered RPMI medium with 10% v/v fetal calf serum (HRF) containing 40 mM EDTA and 200 µg/ml chondroitin sulfate. Cells resuspended in 60 µl HRF were placed in Falcon 2054 tubes (Becton Dickinson, NJ) with 10 µl $^{125}$I-mLIF, then incubated at 4° C. for 3 hr. Non-specific binding was determined as above. Mouse liver membranes were prepared essentially as described[7], solubilised in 1% v/v Triton X-100 (Pierce, IL) and assayed as for LBP. Saturation binding experiments were carried out and Scatchard analysis of the binding isotherm was determined using the curve-fitting program, LIGAND[8], after correction for the bindable fraction of radioligand as previously described[(3)]. Scatchard analysis allows the derivation of the affinity of a labelled ligand for its binding site and the concentration of these binding sites, thereby permitting the quantitation of LBP in samples of known volume, assuming one binding site per LBP molecule and a molecular weight of 90 kDa for LBP.

Bioassay

Samples for bioassay were exchanged into normal saline using prepacked Sephadex G25M (PD10 columns, Pharmacia, Uppsala), concentrated using Centricon-10 microconcentrators (Amicon, MA) and sterilised by passage through a 0.45 µm filter (Millipore, MA). M1 differentiation assays were performed as previously described[9].

Protein Assay

Protein was estimated by the method of Bradford[(13)] using a Coommassie blue based reagent (Pierce, IL) according to the manufacturers instructions.

Amino Acid Sequence Analysis

Amino acid sequence analysis was carried out by Edman degradation of proteins blotted onto a polyvinylidene difluoride (PVDF) membrane as previously described[10].

2. Analysis of LIF Binding Protein

Identification of LIF-binding Activity in Mouse Serum

LIF-binding protein (LBP) was detected in normal mouse sera by its ability to inhibit the binding of $^{125}$I-mLIF to a neutralising monoclonal antibody in a competition radioimmunoassay or to its cellular receptor on 3T3-L1 cells in a competition radioreceptor assay. It was detected by either of these assays in normal mouse sera at a dilution of 1/4 to 1/8, but at a 20 to 30-fold greater dilution in the sera of pregnant mice and a 2–4 fold lower dilution in the sera of neonatal mice (Table 2). Because LIF is a very basic protein, it was important to determine whether this LIF-binding activity was due to a non-specific association of LIF with an acidic serum protein, however a variety of other basic proteins, including lysozyme, α-chymotrypsinogen-A and cytochrome-C, were unable to compete for $^{125}$I-mLIF binding to LBP. In addition, other acute-phase proteins, such as IL-1 and IL-6, were also unable to compete for binding.

Figure 1A:
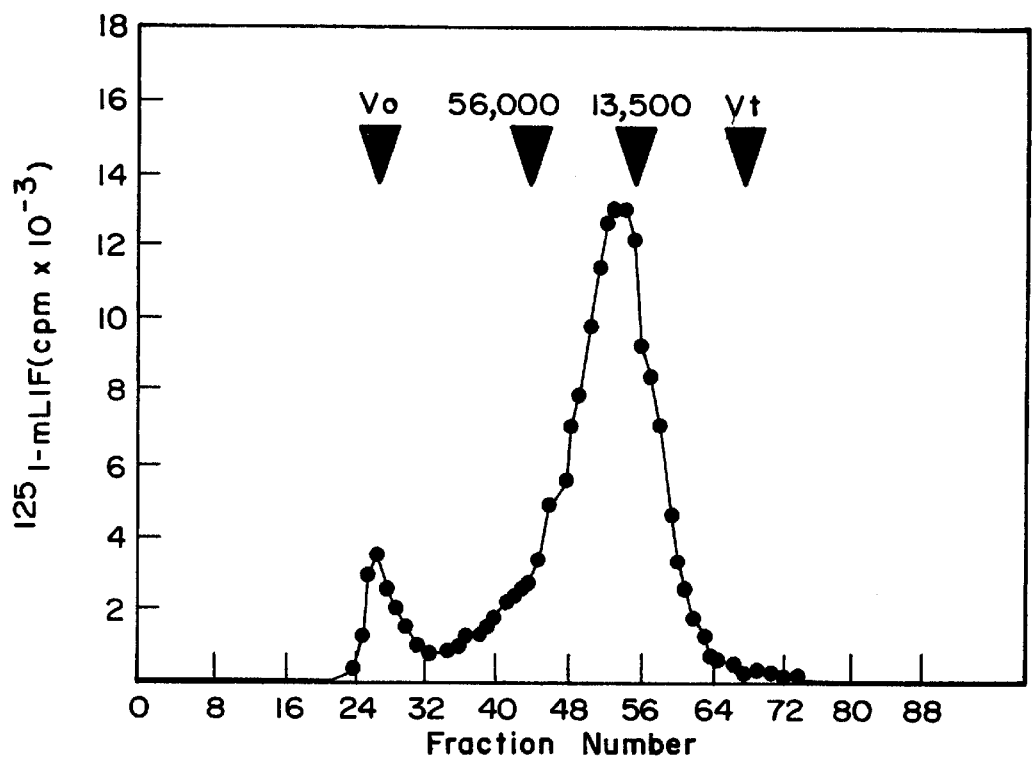
Figure 1B:
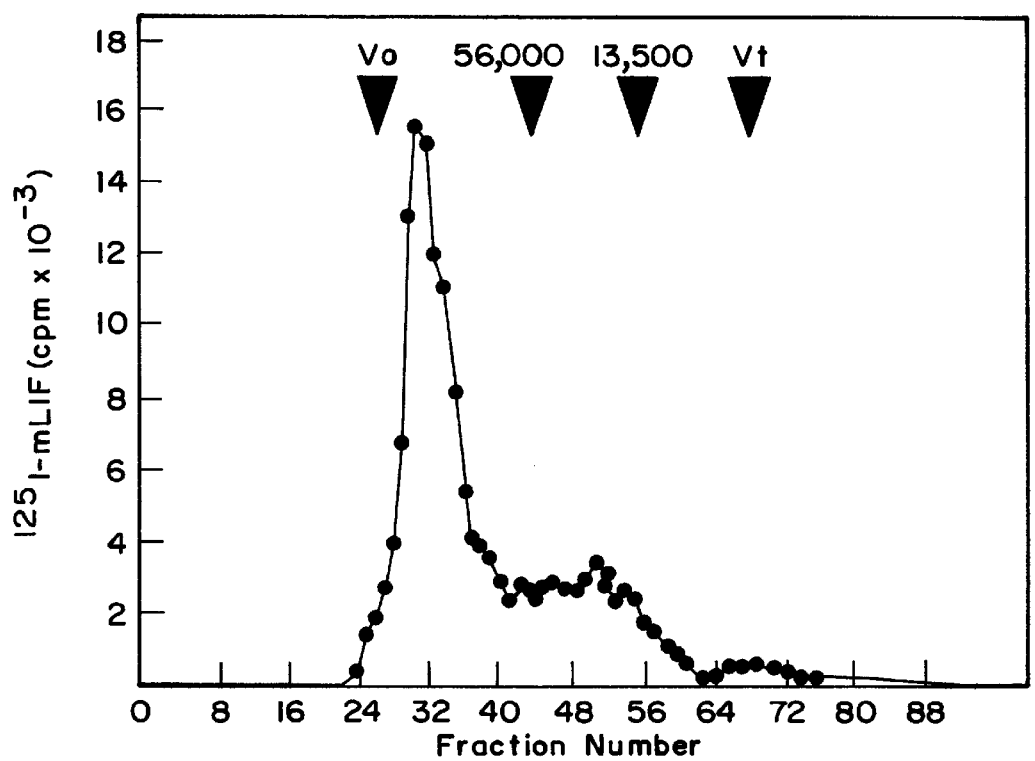

Direct binding of 125I-mLIF to LBP was detected in two different ways. By size-exclusion chromatography, $^{125}$I-mLIF exhibits a molecular weight of approximately 20 kDa. When $^{125}$I-mLIF was chromatographed in the presence of normal mouse serum, under non-dissociating conditions, a labelled complex was detected with an apparent molecular weight of 110 kDa (FIG. 1), signifying that the LIF-binding protein in serum had a molecular weight of about 90 kDa Concanavalin-A Sepharose was demonstrated to have the ability to precipitate the $^{125}$I-mLIF-LBP complex from serum, implying that LBP was a glycoprotein, since the recombinant LIF labelled for these studies was produced in *E. coli* and so contained no carbohydrate groups. This property was used to separate bound from free $^{125}$I-LIF as recently described for solubilised receptor assays[11].

Isolation of LBP

The purification of mLBP from normal mouse sera was achieved by sequential fractionation using affinity chromatography on an immobilised LIF column, anion exchange chromatography, size exclusion chromatography and preparative native polyacrylamide gel electrophoresis (PAGE), as detailed in the methods section, and monitoring LBP by direct $^{125}$I-mLIF binding assays.

LBP was found to be a very unstable protein that was completely inactivated by acidic conditions and in the presence of many of the chemicals usually used in protein purification procedures, such as acetonitrile, methanol, NaDodSO$_4$ and ammonium sulfate. This proved the major difficulty in the isolation of mLBP as it precluded the use of many high-resolution purification techniques, and may be the basis for the relatively low yields obtained during fractionation (Table 3).

Figure 2A:
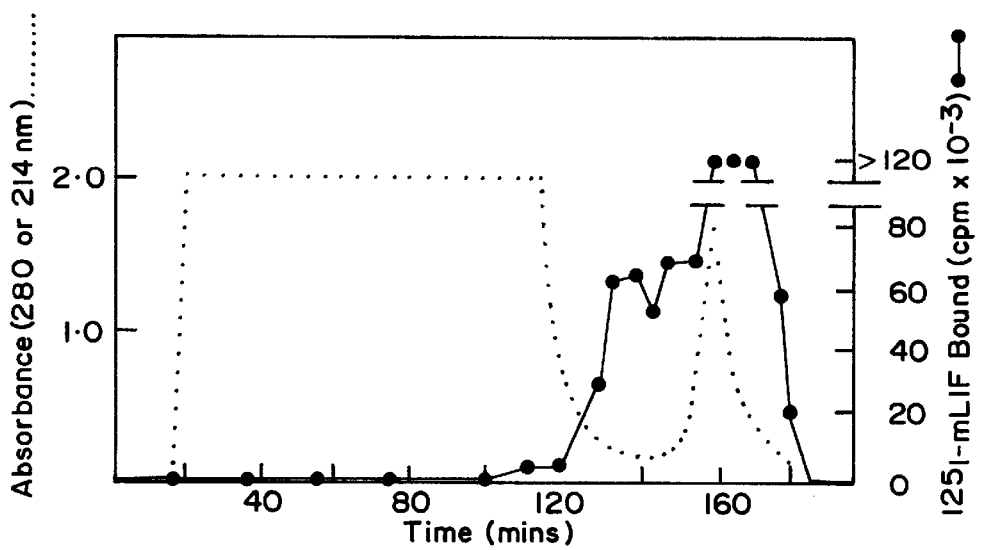
Figure 2B:
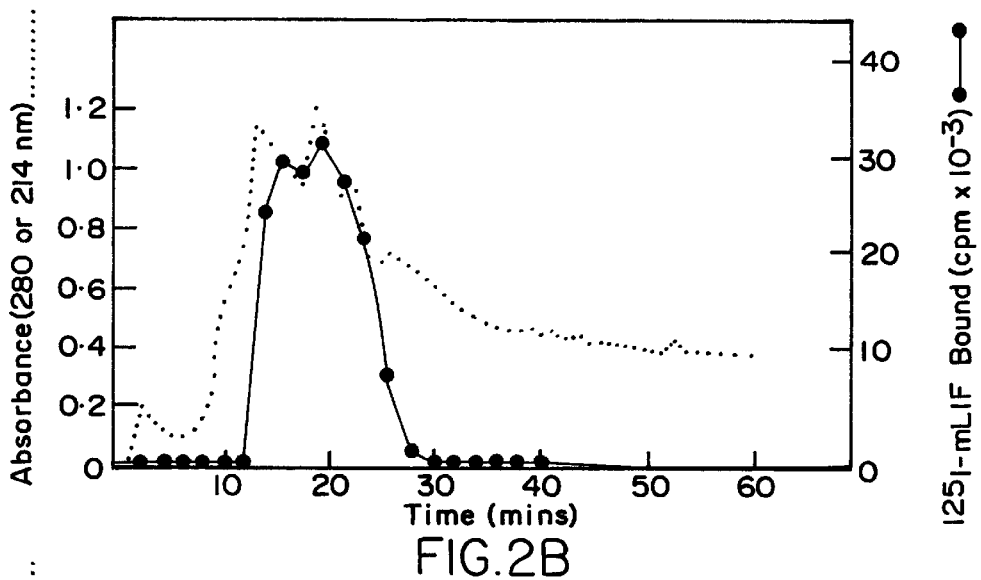
Figure 2C:
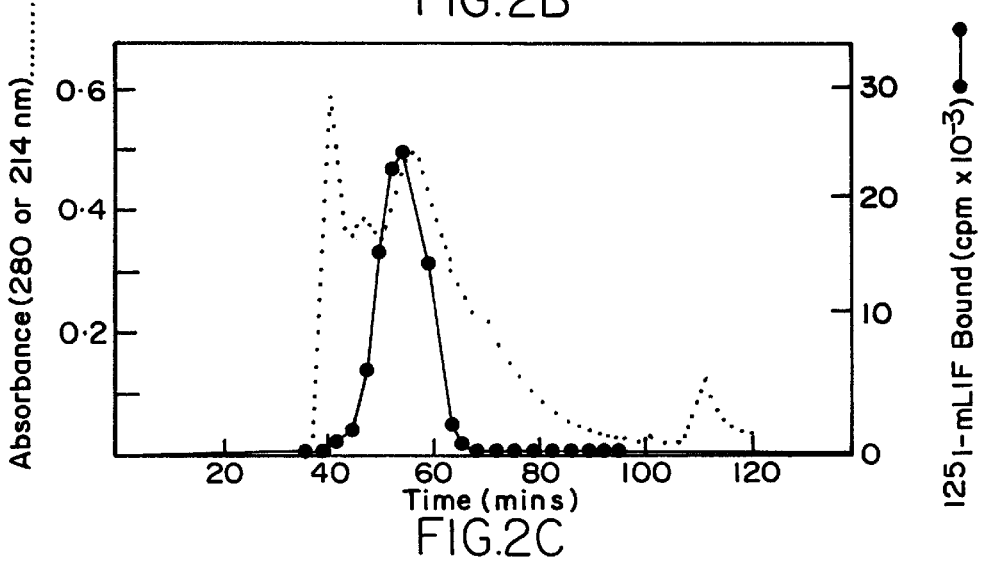

Chemical modification of lysine residues in the LIF molecule has been shown to destroy its biological activity whereas iodination of tyrosine residues is not detrimental to LIF activity[3]. A method of linking protein to Sepharose beads through tyrosine residues was therefore chosen to ensure that the LIF molecule would be active when attached to an affinity column matrix. Affinity chromatography (FIG. 2A) on an mLIF-pABAE Sepharose 4B affinity matrix removed a large proportion of the contaminating serum proteins, although the guanidine used as an eluent had some denaturing effects on LBP activity. A second round of affinity chromatography resulted in a significant additional purification. In contrast, LBP did not bind to a control ovalbumin-pABAE Sepharose 4B column. Anion exchange (FIG. 2B) and size exclusion chromatography (FIG. 2C) confirmed the acidic nature of the protein and its molecular weight of approximately 90 kDa, and achieved a further 1.6-fold purification. Analytical NaDodSO$_4$-PAGE of fractions from the size exclusion column revealed two bands that were barely separated from each other on a 12.5% w/v polyacrylamide gel, but were well separated from other contaminating bands. Both had an apparent molecular weight of approximately 90 kDa and their distributions in size exclusion column fractions and native preparative gel fractions as determined by silver staining of analytical NaDodSO$_4$-PAGE gels exactly matched that of LBP activity by direct $^{125}$I-mLIF binding assay. The two peak fractions were electrophoresed on a 7% w/v NaDodSO$_4$-PAGE gel, blotted onto a PVDF membrane and the two bands of interest were subjected to N-terminal sequencing. The major band had a slightly lower molecular weight and yielded amino acid sequence at the 5 picomole level (23 amino acid residues), while the higher molecular weight band yielded sequence at the 3 picomole level (8 amino acid residues). Both revealed an N-terminal sequence consistent with the following sequence: Gly-Val-Gln-Asp-Leu-Lys-Cys-Thr-Thr-Asn-Asn-Met-Arg-Val-Trp-Asp-Cys-Thr-Trp-Pro-Ala-Pro-Leu (SEQ ID No. 1). The two forms of mLBP were not seen in every preparation and were presumed to be glycosylation variants, although the C-terminus of mLBP is yet to be identified and differences at this end of the molecule could account for the slight size heterogeneity.

Figure 3A:
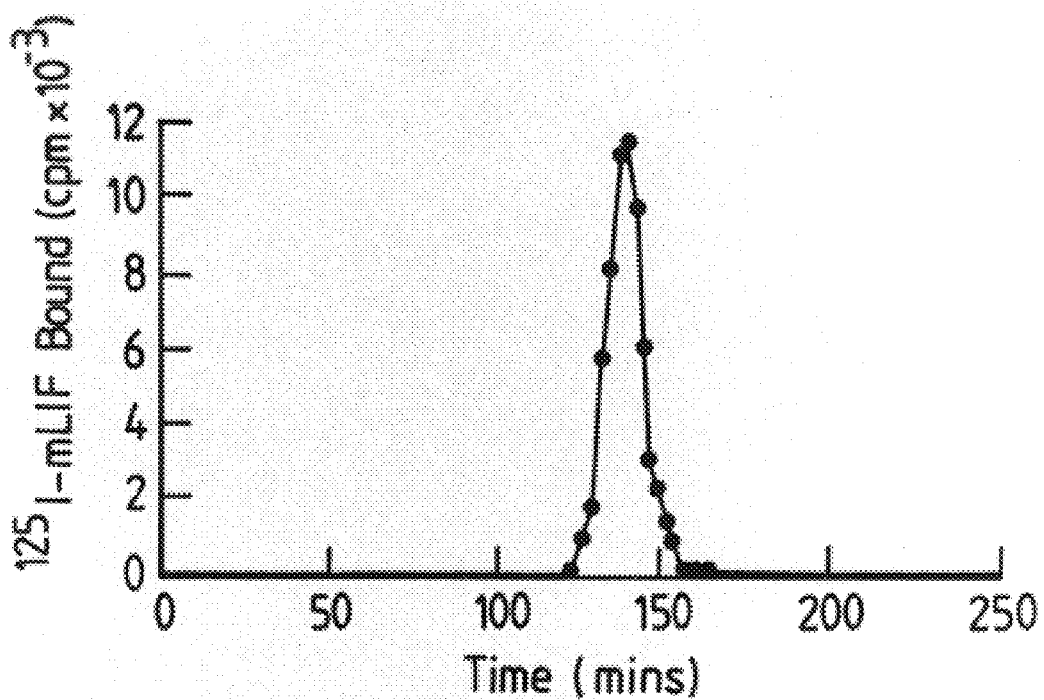
Figure 3B:
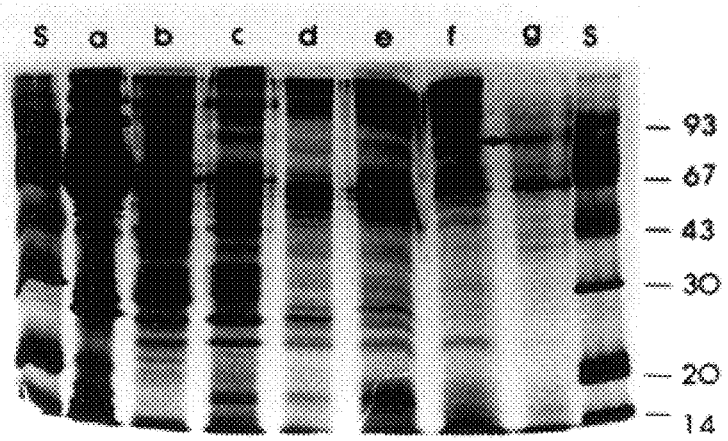

Preparative gel electrophoresis using native conditions (FIG. 3A) allowed high resolution separation of LBP from contaminating proteins with only two major bands of 90 and 67 kDa revealed by analytical NaDodSO$_4$-PAGE after pooling active fractions from this step (FIG. 3B). Fractions pooled from this step were used in assays to determine the binding characteristics of LBP.

Binding Properties of LBP

Figure 4A:
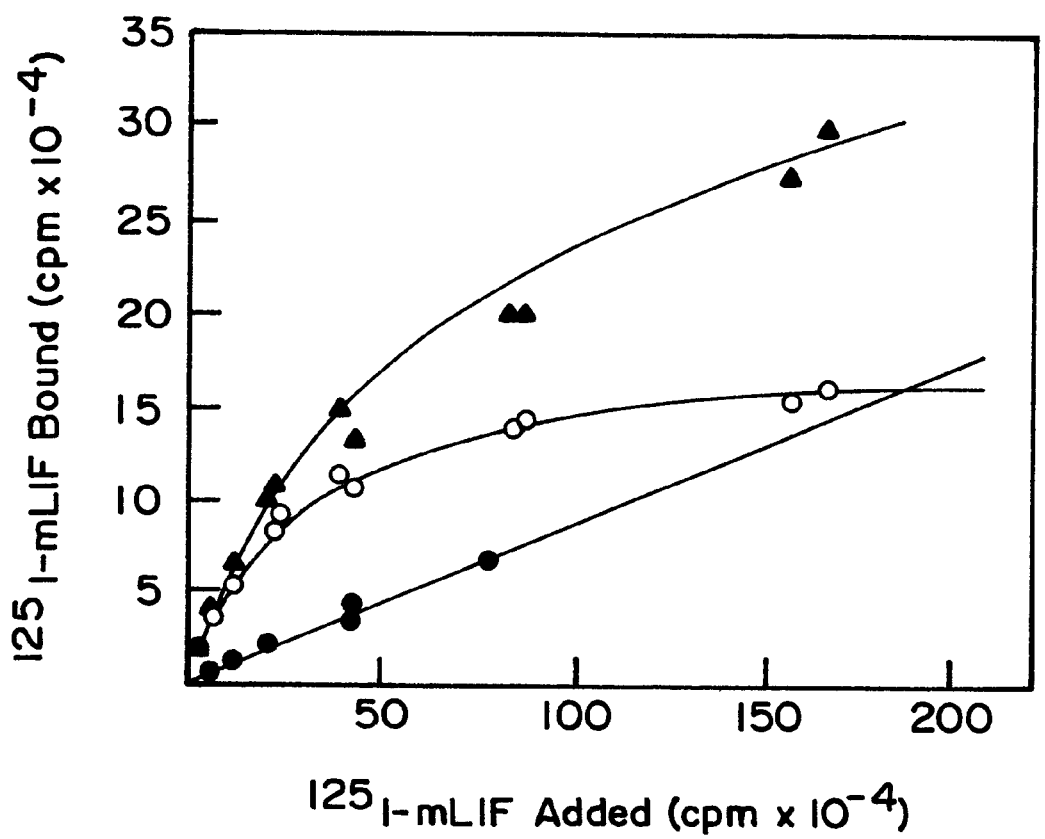
Figure 4B:
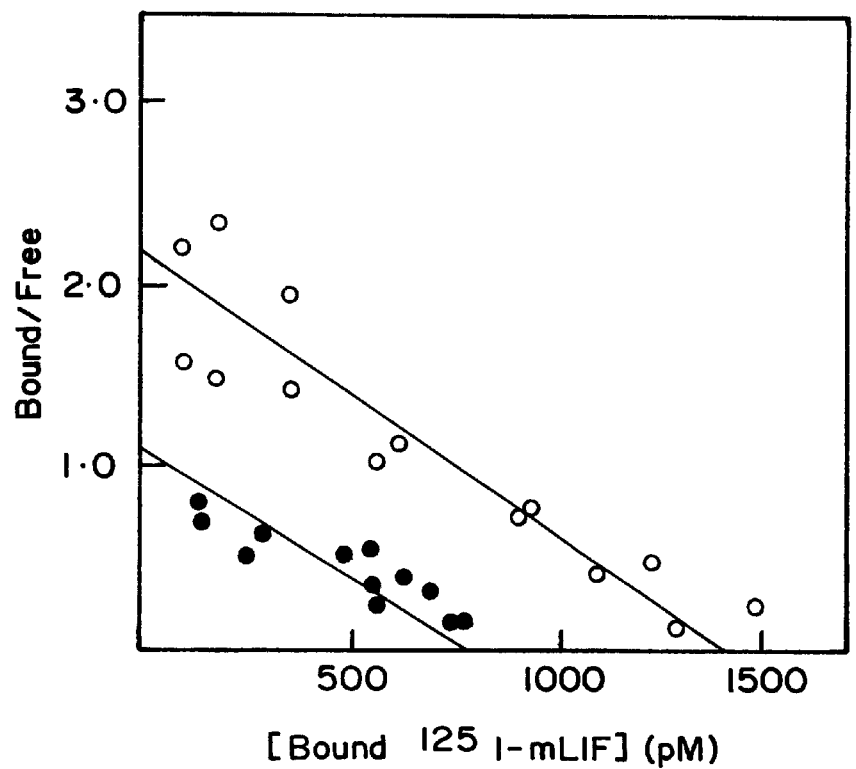
Figure 4C:
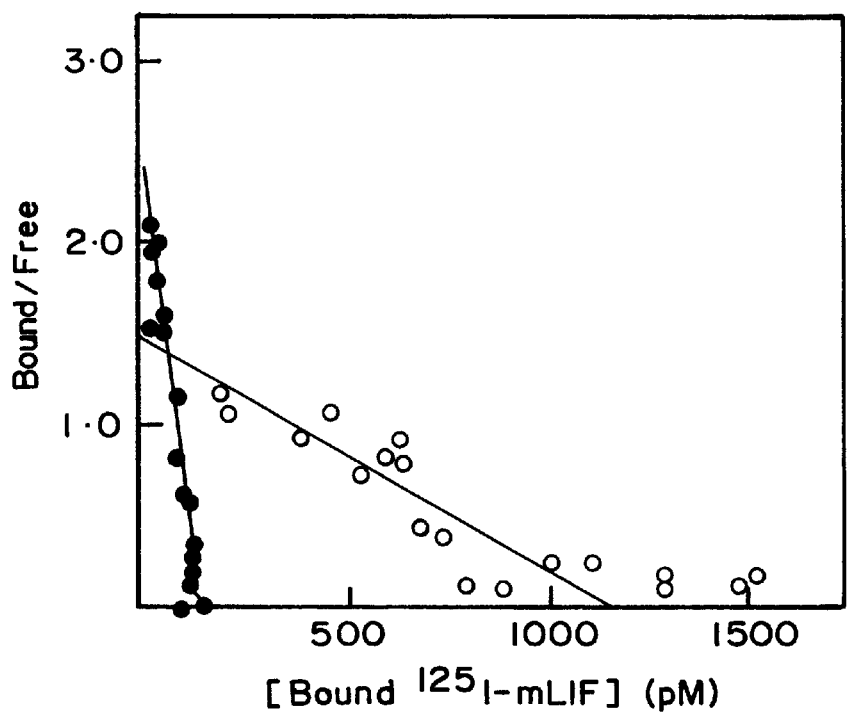

The specific binding of $^{125}$I-mLIF to purified LBP is shown in FIG. 4A Scatchard analysis of the saturation binding isotherm of $^{125}$I-mLIF to normal mouse sera or purified LBP showed that LBP contained a single class of mLIF binding site ($K_D$ 500 pM–3 nM) and indicated that normal mouse serum contains approximately 1–5 µg/ml of LBP (FIG. 4B). The affinity of LBP for mLIF was comparable to that of the low affinity LIF receptor solubilised by detergent from mouse liver membranes ($K_D$=680 pM) and was significantly lower than that of the high affinity cellular receptor on 3T3-L1 cells ($K_D$=57 pM) (FIG. 4C).

Figure 5B:
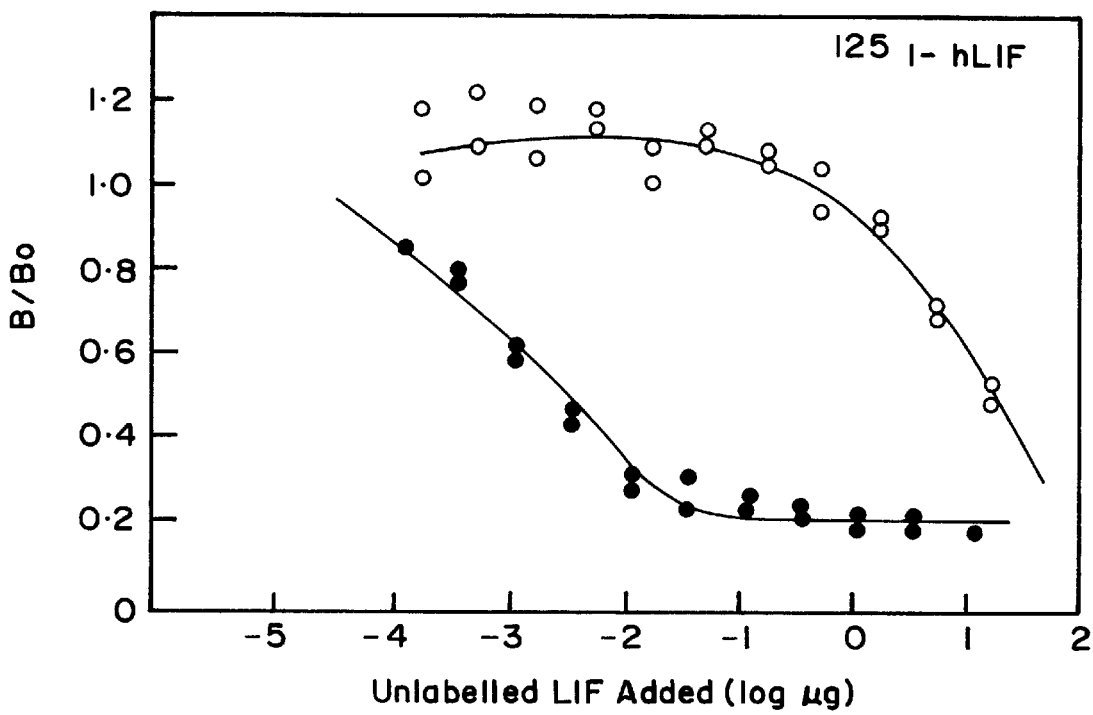

Although hLIF was able to bind to mLBP, its binding characteristics were rather different. Unlabelled mLIF and hLIF showed a similar ability to compete with $^{125}$I-mLIF for binding to mLBP (FIG. 5A), but mLIF was consistently 10,000-fold less effective than hLIF in competing with $^{125}$I-hLIF for binding to mLBP (FIG. 5B).

Blocking Activity of LBP

Figure 6B:
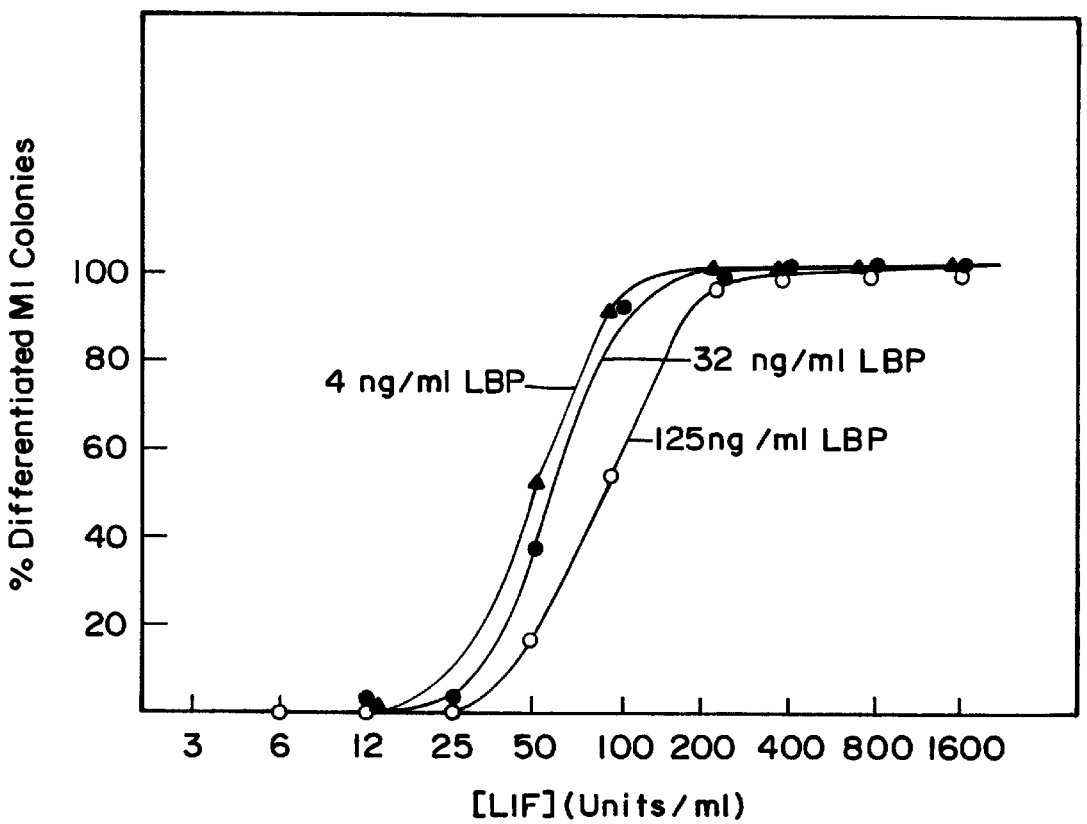

When affinity purified mLBP was combined with mouse LIF in cultures of murine M1 myeloid leukemic cells, it blocked the ability of LIF to induce differentiation of M1 colonies in a dose dependent manner (50% inhibition of 90 U/ml LIF at 62–125 ng/ml LBP). Intermediate doses of mLIF (stimulating 50% differentiation of M1 colonies) revealed inhibition by high doses of LBP, but possibly augmentation at low doses of LBP (2–4 ng/ml) (FIG. 6A). The presence of 125 ng/ml LBP in the culture was able to shift a mLIF titration curve 2-fold towards higher mLIF doses (FIG. 6B).

FIG. 7 shows the blocking of induction of mLIF and hLIF stimulated colonies of M1 leukaemic cells by normal mouse serum. In 1 ml cultures of 300 murine M1 myeloid leukaemic cells, 0.1 ml of serum from normal adult (8 week) C57BL mice was able to block the differentiation-inducing effects after 7 days of incubation of 100 Units of purified recombinant *E. coli*-derived murine LIF (50% blocking with a serum dilution of 1:8) (FIG. 7A). This serum had a greater capacity to block the effects of 800 Units of purified recombinant *E. coli*-derived human LIF (50% blocking with a serum dilution of 1:512). A similar heightened activity in blocking human LIF was seen using purified recombinant human LIF expressed in *E. coli,* CHO cells or in yeast (FIG. 7B).

EXAMPLE 2 m-LIF and hLIF Binding to mLBP

FIG. 8 is a graphical representation showing specific binding of $^{125}$I-m-LIF (A) and $^{125}$I-LIF (B) to mLBP immobilised onto 96 well PVC plates. The results show that mLIF immobilised to a solid support provides a ligand for capturing hLIF in a sample. FIG. 8 shows that hLIF bound to the mLBP at least 20–30 fold better than mLIF as measured by specific binding. Apart from the therapeutic implications on such a finding, these results identify mLBP as a suitable ligand for assaying the presence of hLIF in a biological sample.

EXAMPLE 3

Fusion LBP Polypeptides

Administration of a mouse protein to a human subject may induce an antigenic immune response with therapeutically undesirable consequences. In order to avoid or reduce this potential problem, a protein that is antigenically very similar to a human LBP, but which retains the high-affinity for hLIF that is the particular property of mLBP is constructed. The method used is similar to the method the inventors have previously used to map the site on the hLIF molecule that confers both binding to the hLIF receptor α-chain and the unusual high-affinity binding to the mouse LIF receptor α-chain (mLBP). Using a mLIF molecular framework, the inventors constructed a series of mouse-human LIF chimaeric molecules in order to determine the minimum number of hLIP amino acid residues that it is necessary to substitute into the mLIF sequence in order to create a molecule that has the properties that are peculiar to hLIF (see FIG. 9).

By constructing a series of mouse-human LBP chimaeric molecules using recombinant DNA technology, the minimum number of mLBP amino acid residues is determined that it is necessary to substitute into a hLBP (soluble human LIF receptor α-chain) sequence in order to create a molecule that binds to hLIF with high affinity, as mLBP does, rather than a molecule that binds hLIF with low affinity, as does hLBP (FIG. 10). Recombinant mLBP molecule is anticipated to have identical binding and inhibition properties to the native form of mLBP isolated from normal mouse serum, as all forms of the mouse LIF receptor tested, whether cellular or soluble, have shared the binding properties of mLBP. The ultimate aim is to synthesize a recombinant molecule that is based on the hLIF receptor α-chain amino acid sequence, but is C-terminally truncated so that it is a soluble rather than cell membrane-bound molecule, is of the minimum size that retains LIF-binding properties and is easily expressed in large quantities. In addition, this molecule will contain approximately 5–15 amino acid residues that are substituted for the amino acid residue that is in the identical position in the mouse LIF receptor α-chain amino acid sequence. These substitutions will specifically induce the hLBP molecule to bind hLIF with high affinity, and thus act as an effective hLIF antagonist in vitro or in vivo, however, these few amino acid substitutions would be unlikely to cause the human LBP molecule to become antigenic to the human immune system in vivo.

EXAMPLE 4

Digestion of mLBP with N-glycanase

N-terminal amino acid sequencing of mLBP suggests that it is a truncated form of the cellular LIF receptor α-chain. It is possible to estimate the size of a protein by SDS-PAGE, and correlate this with the predicted molecular weight of the protein, calculated by adding up the individual molecular weights of all the amino acid residues in the amino acid sequence. The mLBP isolated from mouse serum has the ability to bind to a carbohydrate-binding lectin, Concanavalin-A, and so must be a glycosylated molecule. Techniques are not readily available to estimate the proportion of carbohydrate versus protein in a glycosylated protein, so the apparent 90–95 kDa molecular weight of mLBP, as estimated by SDS-PAGE, cannot be correlated with the amino acid sequence.

A second form of mLBP has become apparent in purified preparations of mLBP over time, and is presumed to be formed by proteolytic degradation. This form of mLBP is capable of binding both mLIF and hLIF, and has a molecular weight of approximately 65 kDa as estimated by SDS-PAGE (FIG. 11A,B).

In order to estimate the position of the C-terminus of both the 90–95 kDa and 65 kDa forms of mLBP, preparations containing both these forms were subjected to digestion by N-glycanase, an enzyme that specifically cleaves the bond between an asparagine residue and an N-linked carbohydrate. Digestion was allowed to go to completion and the molecular weights of the deglycosylated proteins were estimated by SDS-PAGE (FIG. 12). The two bands produced by N-glycanase digestion had molecular weights of approximately 63 kDa and 50 kDa, respectively. These bands corresponded to the molecular weights of the protein cores of the two forms of mLBP, without the N-linked carbohydrate, and so could be correlated with the amino acid sequence.

The cellular mLIF receptor comprises two haemopoietin domains, three fibronectin III-like domains, a transmembrane domain and a cytoplasmic domain, and has a glycosylated molecular weight of 190 kDa[12]. The molecular weight of the reported form of the soluble mLIF receptor which consists of two haemopoietin domains and two out of three fibronectin III-like domains is 130 kDa when glycosylated [12] and 75 kDa for the core protein. The predicted molecular weight for the core protein for consisting of two haemopoietin domains and one out of three fibronectin III-like domains is 63 kDa, while for the two haemopoietin domains alone, the predicted molecular weight is 53 kDa. These molecular weights correspond well to the molecular weights of the two deglycosylated forms of mLBP as estimated by SDS-PAGE, which suggests that a variety of forms of mLBP are created by sequential proteolytic removal of fibronectin III-like domains and that each of these forms retains the binding activity described for mLBP.

EXAMPLE 5

Determination of the Amino Acid Sequence of the C-terminus of mLBP

Further information about the C-terminal amino acid sequence of mLBP is obtainable by sequencing proteolytically-produced peptide fragments of mLBP. In order that sequence data can be gained from the different molecular weight forms of mLBP using as little protein as possible, the proteolytic digestion is carried out within an SDS-PAGE gel and the peptides extracted from the gel and separated by reversed-phase HPLC for microsequence analysis.

Briefly, the Coomassie Blue stained band of the correct molecular weight is cut out of the gel and destained with 50% v/v n-propanol containing 3% w/v SDS. The gel slice is then washed extensively with water and dried by centrifugal lyophilization. The gel slice is then rehydrated in 100 μl 0.1M $NaHCO_3$ containing 0.02% v/v Tween-20 and 1–2 μg of protease (for example, trypsin or LysC). Peptides are then extracted from the gel slices with 100 μl 1% v/v trifluoroacetic acid (TFA) for 4 hours, 100 μl 70% v/v TFA for 4 hours, 100 μl 70% v/v TFA for 16 hours and 100 μl 50% v/v TFA/50% acetonitrile for two times 4 hours. The combined eluents are evaporated to near dryness then diluted to 1 ml with 0.1% v/v TFA. The peptides are then separated by reversed-phase HPLC and subjected to amino acid sequence analysis.

TABLE 2

LEVELS OF LBP IN SERUM[1]

| SERUM TYPE | STRAIN | SEX | AGE (wks) | DILUTION GIVING 50% INHIBITION IN RIA | LBP CONC[1] (μg/ml) |
|---|---|---|---|---|---|
| MOUSE | | | | | |
| ADULT | MIXED | MIXED | N/A[3] | 1/4–1/8 | 1 |
| " | C57 | M | 6 | 1/4 | 1 |

TABLE 2-continued

LEVELS OF LBP IN SERUM[1]

| SERUM TYPE | STRAIN | SEX | AGE (wks) | DILUTION GIVING 50% INHIBITION IN RIA | LBP CONC[1] (µg/ml) |
|---|---|---|---|---|---|
| " | C57 | F | 6 | 1/4 | 1 |
| " | CBA | F | 12 | 1/4 | 1 |
| NEONATAL | CBA | F | 1 | 1/2 | 0.5 |
| " | CBA | M | 1 | 1/1 | 0.25 |
| " | CBA | M | 2 | 1/4 | 1 |
| PREGNANT | CBA[2] | F | 12 | 1/128 | 32 |
| HUMAN | N/A[3] | MIXED | N/A[3] | N/D[4] | 0 |
| RAT | N/A[3] | MIXED | N/A[3] | 1/4 | 1 |

[1]Levels of LBP detected in serum expressed as the dilution of serum required to inhibit 50% of specific binding of $^{125}$I-mLIF to a neutralising monoclonal antibody in a competition RIA. The number of $^{125}$I-mLIF binding sites in normal mouse serum was determined by Scatchard analysis to be 1 µg/ml and used as a standard to convert 50% inhibition in RIA to LBP concentration.
[2]14 days pregnant
[3]Not Applicable
[4]Not Detectable

TABLE 3

REPRESENTATIVE PURIFICATION OF LBP FROM NORMAL MOUSE SERUM[1]

| FRACTIONATION PROCEDURE | VOL (ml) | TOTAL LBP (µg) | TOTAL PROTEIN (µg) | YIELD (%) | P[2] (fold) |
|---|---|---|---|---|---|
| Normal Serum | 85 | 102 | $2.24 \times 10^6$ | — | — |
| LIF Sepharose 1 | 78 | 41 | $1.54 \times 10^4$ | 39.8 | 58 |
| LIF Sepharose 2 | 38 | 18 | $2.73 \times 10^3$ | 19.4 | 147 |
| Anion Exchange | 8.9 | 18 | $2.45 \times 10^3$ | 19.9 | 158 |
| Size Exclusion | 3.2 | 6.0 | 573 | 7.8 | 232 |
| Native Gel | 0.8 | 1.4 | 11.6 | 1.4 | 2620 |

[1]Representative purification of LBP from normal mouse serum. Total LBP was calculated from the concentration of $^{125}$I-mLIF binding sites derived from Scatchard analysis, assuming one binding site per LBP molecule and a molecular weight of 90 kDa for LBP.
[2]Purification (fold)

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

REFERENCES

1. Metcalf, D. *Int. J. Cell Cloning* 9: 95–108, 1991.
2. Cuatrecasas, P. and Anfinsen, C. B. *Methods Enzymol* 22: 345–378, 1971.
3. Hilton, D. H., Nicola, N. A. and Metcalf, D. *Proc. Natl. Acad. Sci. USA* 85: 5971–5975, 1988.
4. Laemmli, U. K. *Nature* 227: 680–685, 1970.
5. Butcher, L. A. and Tomkins, J. K. *Anal. Biochem.* 148: 384–388, 1985.
6. Green, H. and Kehinde, O. *Cell* 1: 113–116, 1974.
7. Cuatrecasas, P. *Proc. Natl. Acad. Sci. USA* 69: 318–322, 1972.
8. Munson, P. J. and Rodbard, D. *Anal. Biochem.* 107: 307–310, 1980.
9. Metcalf, D., Hilton, D. J. and Nicola, N. A. *Leukaemia* 2: 216–222, 1990.
10. Ward, L. D., Hong, J., Whitehead, R. H. and Simpson, R. J. *Electrophoresis* 11: 883–891, 1990.
11. Nicola, N. A. and Cary, D. A. *Growth Factors* 6: 119–129, 1992.
12. Gearing, D. P. Thut, C. J. VandenBos, T., Gimpel, S. D., Delaney, P. B., King, J., Price, V., Cosman, D., and Beckman, M. P. *EMBO J.* 10: 2839–2848, 1991
13. Bradford, M. M. *Anal. Biochem.* 72: 248, 1976.
14. Merrifield, J. *Am. Chem. Soc.* 85: 2149, 1964.
15. Sambrook et al *Molecular Cloning: A Laboratory Manual,* Cold Spring Harbor Laboratories, Cold Spring Harbor, N.Y., USA, 1989.

---

What is claimed is:

1. A method of inhibiting the activity of humnan LIF to induce differentiation of human M1 myeloid Leukaemic cells comprising administering to a human an effective amount of mouse Leukaemia Inhibitory Factor (LCF)-binding protein (LBP) in soluble form, said LBP exhibiting at least 20-fold higher binding affinity for human LIF compared to the binding affinity for mouse LIF.

2. A method of inhibiting the activity of human LIF comprising administering to a human an effective amount of a soluble mouse Leukaemia Inhibitory Factor-binding protein (LBP), wherein said mouse LBP exhibits at least 20-fold higher binding affinity for human LIF compared to the binding affinity for mouse LIF.

* * * * *